(12) United States Patent
Aleid et al.

(10) Patent No.: US 10,870,868 B2
(45) Date of Patent: Dec. 22, 2020

(54) METHOD FOR PRODUCING BIOETHANOL FROM DATES

(71) Applicant: KING FAISAL UNIVERSITY, Al-Ahsa (SA)

(72) Inventors: Salah Mohammed Aleid, Alahsa (SA); Siddig Hussein Hamad, Alahsa (SA)

(73) Assignee: KING FAISAL UNIVERSITY, Hofouf (SA)

( * ) Notice: Subject to any disclaimer, the term of this patent is extended or adjusted under 35 U.S.C. 154(b) by 5 days.

(21) Appl. No.: 16/391,497

(22) Filed: Apr. 23, 2019

(65) Prior Publication Data

US 2020/0340018 A1 Oct. 29, 2020

(51) Int. Cl.
| | | |
|---|---|---|
| *C12P 7/08* | (2006.01) |
| *C12N 1/16* | (2006.01) |
| *C12M 1/00* | (2006.01) |
| *C12M 1/33* | (2006.01) |
| *C12M 1/34* | (2006.01) |
| *C12M 1/24* | (2006.01) |

(52) U.S. Cl.
CPC ............... *C12P 7/08* (2013.01); *C12M 21/12* (2013.01); *C12M 45/02* (2013.01); *C12N 1/16* (2013.01); *C12M 23/08* (2013.01); *C12M 41/36* (2013.01)

(58) Field of Classification Search
None
See application file for complete search history.

(56) References Cited

U.S. PATENT DOCUMENTS

| | | |
|---|---|---|
| 8,530,211 B2 | 9/2013 | Jeffries et al. |
| 2009/0226993 A1 | 9/2009 | Kumar et al. |
| 2011/0027846 A1 | 2/2011 | De Sa |

FOREIGN PATENT DOCUMENTS

| | | |
|---|---|---|
| CN | 10475966 A | 7/2009 |
| CN | 106967757 A | 7/2017 |
| WO | 2009001205 A2 | 12/2008 |
| WO | 2009069323 A1 | 6/2009 |
| WO | 2017116840 A1 | 7/2017 |

OTHER PUBLICATIONS

Zohri, A. et al. Mycobiology 2000 vol. 28, pp. 76-81.*
Vu, D. et al., Studies in Mycology 2016 vol. 85, pp. 91-105.*
Chniti, S. et al., Biomass and Bioenergy 2014 vol. 69, pp. 66-70.*
Pimpakan, P. et al., Kasetsart J. (Nat. Sci.) 2012, vol. 46, pp. 582-591.*
Taouda, H., "Biomass and bio-ethanol production from date extract", JMES, 8(9): pp. 3093-3098, (2017).
International Search Report and Written Opinion for PCT/IB2020/053665, dated Jul. 23, 2020.
Ponthein, W. and Cheirsilp, B., "Development of Acetone Butanol Ethanol (ABE) Production from Palm Pressed Fiber by Mixed Culture of *Clostridium* sp. and *Bacillus* sp.," Energy Procedia 9 pp. 459-467 (2011).
Abd-Alla, M. H. et al., "Acetone-butanol-ethanol production from substandard and surplus dates by Egyptian native Clostridium strains," Anaerobe 32, pp. 77-86 (2015).

* cited by examiner

*Primary Examiner* — Heidi Reese
(74) *Attorney, Agent, or Firm* — Nath, Goldberg & Meyer; Richard C. Litman

(57) ABSTRACT

The method for producing bioethanol from dates includes manufacturing a suitable substrate for bioethanol from dates and fermenting the date substrate to produce bioethanol. The date substrate may be produced by de-pitting date fruits, heating the flesh with water to produce a mixture, filter pressing the mixture to produce a juice, and concentrated by vacuum drying to produce a date substrate. The date substrate may then be fermented in either a batch or a fed-batch culture. The fermentation may be performed with a thermophilic yeast, such *K. marxianus*. In an alternative embodiment the date substrate may be a date fruit extract.

10 Claims, 14 Drawing Sheets

Specification includes a Sequence Listing.

SEQUENCE LISTING

<160> NUMBER OF SEQ ID NOS: 16

<210> SEQ ID NO 1
<211> LENGTH: 17
<212> TYPE: DNA
<213> ORGANISM: Artificial Sequence
<220> FEATURE:
<223> OTHER INFORMATION: primer

<400> SEQUENCE: 1
acccgctgaa cttaagc                                                    17

<210> SEQ ID NO 2
<211> LENGTH: 17
<212> TYPE: DNA
<213> ORGANISM: Artificial Sequence
<220> FEATURE:
<223> OTHER INFORMATION: Primer

<400> SEQUENCE: 2
tcctgaggga aacttcg                                                    17

<210> SEQ ID NO 3
<211> LENGTH: 22
<212> TYPE: DNA
<213> ORGANISM: Artificial Sequence
<220> FEATURE:
<223> OTHER INFORMATION: primer

<400> SEQUENCE: 3
gcattcccaa acaactcgac tc                                              22

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttacgtccct gccctttgta                                                 20

<210> SEQ ID NO 5
<211> LENGTH: 1000
<212> TYPE: DNA
<213> ORGANISM: Kluyveromyces marxianus

<400> SEQUENCE: 5

```
ttagtgaggc ctcaggattt gcttagagaa gggggcaact ccatctcaga gcgaaaaatc    60
tggtcaaact tggtcattta gaggaactaa aagtcgtaac aaggtttccg taggtgaacc   120
tgcggaagga tcattaaaga ttatgaatga atagattact gggggaatcg tctgaacaag   180
gcctgcgctt aattgcgcgg ccagttcttg attctctgct atcagttttc tatttctcat   240
cctaaacaca atgagttttt ttctctatga actacttccc tggagagctc gtctctccag   300
tggacataaa cacaaacaat attttgtatt atgaaaaact attatactat aaaatttaat   360
attcaaaact ttcaacaacg gatctcttgg ttctcgcatc gatgaagaac gcagcgaatt   420
gcgatatgta ttgtgaattg cagattttcg tgaatcatca aatctttgaa cgcacattgc   480
gccctctggt attccagggg gcatgcctgt ttgagcgtca tttctctctc aaacctttgg   540
gtttggtagt gagtgatact cgtctcgggt taacttgaaa gtggctagcc gttgccatct   600
gcgtgagcag ggctgcgtgt caagtctatg gactcgactc ttgcacatct acgtcttagg   660
tttgcgccaa ttcgtggtaa gcttgggtca tagagactca taggtgttat aaagactcgc   720
tggtgtttgt ctccttgagg catacggctt taaccaaaac tctcaaagtt tgacctcaaa   780
tcaggtagga gtaccgctg aacttaagca tatcaataag cggaggaaaa gaaaccaacc    840
gggattgcct tagtaacggc gagtgaagcg gcaaaagctc aaatttgaaa tctggcgtct   900
tcgacgtccg agttgtaatt tgaagaaggc gactttgtag ctggtccttg tctatgttcc   960
ttggaacagg acgtcataga gggtgagaat cccgtgtggc                        1000
```

<210> SEQ ID NO 6
<211> LENGTH: 800
<212> TYPE: DNA
<213> ORGANISM: Kluyveromyces marxianus

<400> SEQUENCE: 6

```
ttagtacggc gaagtgaagc ggcaaaagct caaatttgaa atctggcgtc ttcgacgtcc    60
gagttgtaat ttgaagaagg cgactttgta gctggtcctt gtctatgttc cttggaacag   120
gacgtcatag agggtgagaa tcccgtgtgg cgaggatccc agttatttgt aaagtgcttt   180
cgacgagtcg agttgtttgg gaatgcagct ctaagtgggt ggtaaattcc atctaaagct   240
aaatattggc gagagaccga tagcgaacaa gtacagtgat ggaaagatga aaagaacttt   300
gaaaagagag tgaaaaagta cgtgaaattg ttgaaggga agggcatttg atcagacatg   360
gcgtttgctt cggctttcgc tgggccagca tcagttttag cggttggata atcctcggg    420
aatgtggctc tgcttcggta gagtgttata gcccgtggga atacagccag ctgggactga   480
ggattgcgac ttttgtcaag gatgctgcg taatggttaa atgccgcccg tcttgaaaca    540
cggaccaagg agtctaacgt ctatgcgagt gtttgggtgt aaacccgta cgcgtaatga    600
aagtgaacgt aggtgagggc ccgcaagggt gcatcatcga ccgatcctga tgtcttcgga   660
tggatttgag taagagcata gctgtttgga cccgaaagat ggtgaactat gcctgaatag   720
ggtgaagcca gaggaaactc tggtggaggc tcgtagcggt tctgacgtgc aaatcgatcg   780
tcgaatttgg gtatagggcg                                              800
```

<210> SEQ ID NO 7

<211> LENGTH: 1000
<212> TYPE: DNA
<213> ORGANISM: Kluyveromyces marxianus

<400> SEQUENCE: 7

```
ttagtgaggc ctcaggattt gcttagagaa gggggcaact ccatctcaga gcgaaaaatc      60
tggtcaaact tggtcattta gaggaactaa aagtcgtaac aaggtttccg taggtgaacc     120
tgcggaagga tcattaaaga ttatgaatga atagattact gggggaatcg tctgaacaag     180
gcctgcgctt aattgcgcgg ccagttcttg attctctgct atcagttttc tatttctcat     240
cctaaacaca atggagtttt ttctctatga actacttccc tggagagctc gtctctccag     300
tggacataaa cacaaacaat attttgtatt atgaaaaact attatactat aaaatttaat     360
attcaaaact ttcaacaacg gatctcttgg ttctcgcatc gatgaagaac gcagcgaatt     420
gcgatatgta ttgtgaattg cagattttcg tgaatcatca aatctttgaa cgcacattgc     480
gccctctggt attccagggg gcatgcctgt tgagcgtca tttctctctc aaacctttgg     540
gtttggtagt gagtgatact cgtctcgggt aacttgaaa gtggctagcc gttgccatct     600
gcgtgagcag ggctgcgtgt caagtctatg actcgactc ttgcacatct acgtcttagg     660
tttgcgccaa ttcgtggtaa gcttgggtca tagagactca taggtgttat aaagactcgc     720
tggtgtttgt ctccttgagg catacggctt taaccaaaac tctcaaagtt tgacctcaaa     780
tcaggtagga gtacccgctg aacttaagca tatcaataag cggaggaaaa gaaaccaacc     840
gggattgcct tagtaacggc gagtgaagcg gcaaaagctc aaatttgaaa tctggcgtct     900
tcgacgtccg agttgtaatt tgaagaaggc gactttgtag ctggtccttg tctatgttcc     960
ttggaacagg acgtcataga gggtgagaat cccgtgtggc                          1000
```

<210> SEQ ID NO 8
<211> LENGTH: 800
<212> TYPE: DNA
<213> ORGANISM: Kluyveromyces marxianus

<400> SEQUENCE: 8

```
cttagtacgg cgagtgaagc ggcaaaagct caaatttgaa atctggcgtc ttcgacgtcc      60
gagttgtaat ttgaagaagg cgactttgta gctggtcctt gtctatgttc cttggaacag     120
gacgtcatag agggtgagaa tcccgtgtgg cgaggatccc agttatttgt aaagtgcttt     180
cgacgagtcg agttgtttgg gaatgcagct ctaagtgggt ggtaaattcc atctaaagct     240
aaatattggc gagagaccga tagcgaacaa gtacagtgat ggaaagatga aaagaacttt     300
gaaaagagag tgaaaaagta cgtgaaattg ttgaagggga agggcatttg atcagacatg     360
gcgtttgctt cggctttcgc tgggccagca tcagttttag cggttggata atcctcggg      420
aatgtggctc tgcttcggta gagtgttata gcccgtggga atacagccag ctgggactga     480
ggattgcgac ttttgtcaag gatgctggcg taatggttaa atgccgcccg tcttgaaaca     540
cggaccaagg agtctaacgt ctatgcgagt gtttgggtgt aaaacccgta cgcgtaatga     600
aagtgaacgt aggtgagggc ccgcaagggt gcatcatcga ccgatcctga tgtcttcgga     660
tggatttgag taagagcata gctgttggga cccgaaagat ggtgaactat gcctgaatag     720
ggtgaagcca gaggaaactc tggtggaggc tcgtagcggt tctgacgtgc aaatcgatcg     780
tcgaatttgg gtatagggcg                                                 800
```

<210> SEQ ID NO 9
<211> LENGTH: 1000

```
<212> TYPE: DNA
<213> ORGANISM: Kluyveromyces marxianus

<400> SEQUENCE: 9
tagtgaggcc tcaggatttg ctttagagaa gggggcaact tccatctcag tgcgaaaaat      60
ctggtcaaac ttggtcattt agaggaacta aaagtcgtaa caaggtttcc gtaggtgaac     120
ctgcggaagg atcattaaag attatgaatg aatagattac tgggggaatc gtctgaacaa     180
ggcctgcgct taattgcgcg ccagttcctt gattctctgc tatcagtttt ctatttctca     240
tcctaaacac aatggagttt tttctctatg aactacttcc ctggagagct cgtctctcca     300
gtggacataa acacaaacaa tatttttgtat atgaaaaac tattatacta taaaatttaa     360
tattcaaaac tttcaacaac ggatctcttg gttctcgcat cgatgaagaa cgcagcgaat     420
tgcgatatgt attgtgaatt gcagattttc gtgaatcatc aaatctttga acgcacattg     480
cgccctctgg tattccaggg ggcatgcctg tttgagcgtc atttctctct caaacctttg     540
ggtttggtag tgagtgatac tcgtctcggg ttaacttgaa agtggctagc cgttgccatc     600
tgcgtgagca gggctgcgtg tcaagtctat ggactcgact cttgcacatc tacgtcttag     660
gtttgcgcca attcgtggta agcttgggtc atagagactc ataggtgtta taaagactcg     720
ctggtgtttg tctccttgag gcatacggct ttaaccaaaa ctctcaaagt ttgacctcaa     780
atcaggtagg agtacccgct gaacttaagc atatcaataa gcggaggaaa agaaaccaac     840
cgggattgcc ttagtaacgg cgagtgaagc ggcaaaagct caaatttgaa atctggcgtc     900
ttcgacgtcc gagttgtaat ttgaagaagg cgactttgta gctggtcctt gtctatgttc     960
cttggaacag gacgtcatag agggtgagaa tcccgtgtgg                          1000

<210> SEQ ID NO 10
<211> LENGTH: 800
<212> TYPE: DNA
<213> ORGANISM: Kluyveromyces marxianus

<400> SEQUENCE: 10
ttagtacggc gtagtgaagc ggcaaaagct caaatttgaa atctggcgtc ttcgacgtcc      60
gagttgtaat ttgaagaagg cgactttgta gctggtcctt gtctatgttc cttggaacag     120
gacgtcatag agggtgagaa tcccgtgtgg cgaggatccc agttattgt aaagtgcttt     180
cgacgagtcg agttgtttgg gaatgcagct ctaagtgggt ggtaaattcc atctaaagct     240
aaatattggc gagagaccga tagcgaacaa gtacagtgat ggaaagatga aaagaacttt     300
gaaaagagag tgaaaagta cgtgaaattg ttgaaaggga agggcatttg atcagacatg     360
gcgtttgctt cggcttccgc tgggccagca tcagttttag cggttggata aatcctcggg     420
aatgtggctc tgcttcggta gagtgttata gcccgtggga atacagccag ctgggactga     480
ggattgcgac ttttgtcaag gatgctggcg taatggttaa atgccgcccg tcttgaaaca     540
cggaccaagt agtctaacgt ctatgcgagt gtttgggtgt aaaacccgta cgcgtaatga     600
aagtgaacgt aggtgagggc ccgcaagggt gcatcatcga ccgatcctga tgtcttcgga     660
tggatttgag taagagcata gctgttggga cccgaaagat ggtgaactat gcctgaatag     720
ggtgaagcca ggaaaactc tggtggaggc tcgtagcggt tactgacgtg caaatcgatc     780
gtcgaatttg ggtataggc                                                 800

<210> SEQ ID NO 11
<211> LENGTH: 1000
<212> TYPE: DNA
```

<213> ORGANISM: Kluyveromyces marxianus

<400> SEQUENCE: 11

```
gtgaggcctc aggatttgct tagagaaggg ggcaactcca tctcagagcg aaaaatctgg      60
tcaaacttgg tcatttagag gaactaaaag tcgtaacaag gtttccgtag gtgaacctgc     120
ggaaggatca ttaaagatta tgaatgaata gattactggg ggaatcgtct gaacaaggcc     180
tgcgcttaat tgcgcggcca gttcttgatt ctctgctatc agttttctat ttctcatcct     240
aaacacaatg gagttttttc tctatgaact acttccctgg agagctcgtc tctccagtgg     300
acataaacac aaacaatatt ttgtattatg aaaaactatt atactataaa atttaatatt     360
caaaactttc aacaacggat ctcttggttc tcgcatcgat gaagaacgca gcgaattgcg     420
atatgtattg tgaattgcag attttcgtga atcatcaaat cttttgaacgc acattgcgcc     480
ctctggtatt ccaggggggca tgcctgtttg agcgtcattt ctctctcaaa cctttgggtt     540
tggtagtgag tgatactcgt ctcgggttaa cttgaaagtg gctagccgtt gccatctgcg     600
tgagcagggc tgcgtgtcaa gtctatggac tcgactcttg cacatctacg tcttaggttt     660
gcgccaattc gtggtaagct tgggtcatag agactcatag gtgttataaa gactcgctgg     720
tgtttgtctc cttgaggcat acggcttaa ccaaaactct caaagtttga cctcaaatca     780
ggtaggagta cccgctgaac ttaagcatat caataagcgg aggaaaagaa accaaccggg     840
attgccttag taacggcgag tgaagcggca aaagctcaaa tttgaaatct ggcgtcttcg     900
acgtccgagt tgtaatttga agaaggcgac tttgtagctg gtcctttgtc tatgttcctt     960
ggaacaagga cgtcataaga agggtgagaa tcccgtgtgg                         1000
```

<210> SEQ ID NO 12
<211> LENGTH: 800
<212> TYPE: DNA
<213> ORGANISM: Kluyveromyces marxianus

<400> SEQUENCE: 12

```
cttagtacgg cgtagtgaag cggcaaaagc tcaaatttga atctggcgt cttcgacgtc      60
cgagttgtaa tttgaagaag gcgacttttgt agctggtcct tgtctatgtt ccttggaaca    120
ggacgtcata gagggtgaga atcccgtgtg gcgaggatcc cagttatttg taaagtgctt    180
tcgacgagtc gagttgtttg gaatgcagc tctaagtggg tggtaaattc catctaaagc     240
taaatattgg cgagagaccg atagcgaaca agtacagtga tggaaagatg aaaagaactt     300
tgaaaagaga gtgaaaaagt acgtgaaatt gttgaaaggg aagggcattt gatcagacat    360
ggcgttttgct tcggctttcg ctgggccagc atcagttttta gcggttggat aaatcctcgg    420
gaatgtggct ctgcttcggt agagtgttat agcccgtggg aatacagcca gctgggactg    480
aggattgcga cttttgtcaa ggatgctggc gtaatggtta aatgccgccc gtcttgaaac    540
acggaccaag gagtctaacg tctatgcgag tgtttgggtg taaaacccgt acgcgtaatg    600
aaagtgaacg taggtgaggg cccgcaaggg tgcatcatcg accgatcctg atgtcttcgg    660
atggatttga gtaagagcat agctgttggg acccgaaaga tggtgaacta tgcctgaata    720
gggtgaagcc agaggaaact ctggtggagg ctcgtagcgg ttctgacgtg caaatcgatc    780
gtcgaatttg ggtatagggc                                               800
```

<210> SEQ ID NO 13
<211> LENGTH: 1000
<212> TYPE: DNA
<213> ORGANISM: Kluyveromyces marxianus

<400> SEQUENCE: 13

```
ttagtgaggc tcaggatttt gcttagagaa gggggcaact ccatctcaga gcgaaaaatc      60
tggtcaaact tggtcattta gaggaactaa aagtcgtaac aaggtttccg taggtgaacc     120
tgcggaagga tcattaaaga ttatgaatga atagattact gggggaatcg tctgaacaag     180
gcctgcgctt aattgcgcgg ccagttcttg attctctgct atcagttttc tatttctcat     240
cctaaacaca atggagtttt ttctctatga actacttccc tggagagctc gtctctccag     300
tggacataaa cacaaacaat attttgtatt atgaaaaact attatactat aaaatttaat     360
attcaaaact ttcaacaacg gatctcttgg ttctcgcatc gatgaagaac gcagcgaatt     420
gcgatatgta ttgtgaattg cagattttcg tgaatcatca aatctttgaa cgcacattgc     480
gccctctggt attccagggg gcatgcctgt ttgagcgtca tttctctctc aaacctttgg     540
gtttggtagt gagtgatact cgtctcgggt taacttgaaa gtggctagcc gttgccatct     600
gcgtgagcag ggctgcgtgt caagtctatg gactcgactc ttgcacatct acgtcttagg     660
tttgcgccaa ttcgtggtaa gcttgggtca tagagactca taggtgttat aaagactcgc     720
tggtgtttgt ctccttgagg catacggctt taaccaaaac tctcaaagtt tgacctcaaa     780
tcaggtagga gtacccgctg aacttaagca tatcaataag cggaggaaaa gaaaccaacc     840
gggattgcct tagtaacggc gagtgaagcg gcaaaagctc aaatttgaaa tctggcgtct     900
tcgacgtccg agttgtaatt tgaagaaggc gactttgtag ctggtccttg tctatgttcc     960
ttggaacagg acgtcataga gggtgagaat cccgtgtggc                          1000
```

<210> SEQ ID NO 14
<211> LENGTH: 820
<212> TYPE: DNA
<213> ORGANISM: Kluyveromyces marxianus

<400> SEQUENCE: 14

```
gacaccggga tgccttagta acggcgaagt gaagcggcaa aagctcaaat ttgaaatctg      60
gcgtcttcga cgtccgagtt gtaatttgaa gaaggcgact ttgtagctgg tccttgtcta     120
tgttccttgg aacaggacgt catagagggt gagaatcccg tgtggcgagg atcccagtta     180
tttgtaaagt gctttcgacg agtcgagttg tttgggaatg cagctctaag tgggtggtaa     240
attccatcta aagctaaata ttggcagaga accgatagcg aacaagtaca gtgatggaaa     300
gatgaaaaga actttgaaaa gagagtgaaa aagtacgtga aattgttgaa agggaagggc     360
atttgatcag acatggcgtt tgcttcggct ttcgctgggc cagcatcagt tttagcggtt     420
ggataaatcc tcgggaatgt ggctctgctt cggtagagtg ttatagcccg tgggaataca     480
gccagctggg actgaggatt gcacttttg tcaaggatgc tggcgtaatg gttaaatgcc     540
gcccgtcttg aaacacggac caaggagtct aacgtctatg cgagtgtttg ggtgtaaaac     600
ccgtacgcgt aatgaaagtg aacgtaggtg agggcccgca aggtgcatc atcgaccgat     660
cctgatgtct tcggatggat ttgagtaaga gcatagctgt tgggacccga agatggtga     720
actatgcctg aataggggtga agccagagga aactctggtg gaggctcgta gcggttctga     780
cgtgcaaatc gatcgtcgaa tttgggtata gggcgaaaga                           820
```

<210> SEQ ID NO 15
<211> LENGTH: 1000
<212> TYPE: DNA
<213> ORGANISM: Kluyveromyces marxianus

```
<400> SEQUENCE: 15
tagtgaggcc tcaggatttg cttagagaag ggggcaactc catctcagag cgaaaaatct    60
ggtcaaactt ggtcatttag aggaactaaa agtcgtaaca aggtttccgt aggtgaacct   120
gcggaaggat cattaaagat tatgaatgaa tagattactg ggggaatcgt ctgaacaagg   180
cctgcgctta attgcgcggc cagttcttga ttctctgcta tcagttttct atttctcatc   240
ctaaacacaa tggagttttt tctctatgaa ctacttccct ggagagctcg tctctccagt   300
ggacataaac acaaacaata ttttgtatta tgaaaaacta ttatactata aaatttaata   360
ttcaaaactt tcaacaacgg atctcttggt tctcgcatcg atgaagaacg cagcgaattg   420
cgatatgtat tgtgaattgc agattttcgt gaatcatcaa atctttgaac gcacattgcg   480
ccctctggta ttccaggggg catgcctgtt tgagcgtcat ttctctctca aacctttggg   540
tttggtagtg agtgatactc gtctcgggtt aacttgaaag tggctagccg ttgccatctg   600
cgtgagcagg gctgcgtgtc aagtctatgg actcgactct tgcacatcta cgtcttaggt   660
ttgcgccaat tcgtggtaag cttgggtcat agagactcat aggtgttata aagactcgct   720
ggtgtttgtc tccttgaggc atacggcttt aaccaaaact ctcaaagttt gacctcaaat   780
caggtaggag tacccgctga acttaagcat atcaataagc ggaggaaaag aaaccaaccg   840
ggattgcctt agtaacggcg agtgaagcgg caaaagctca aatttgaaat ctggcgtctt   900
cgacgtccga gttgtaattt gaagaaggcg actttgtagc tggtccttgt ctatgttcct   960
tggaacagga cgtcatagag ggtgagaatc ccgtgtggcg                        1000

<210> SEQ ID NO 16
<211> LENGTH: 800
<212> TYPE: DNA
<213> ORGANISM: Kluyveromyces marxianus

<400> SEQUENCE: 16
ttagtacggc gagtgaagcg gcaaaagctc aaatttgaaa tctggcgtct tcgacgtccg    60
agttgtaatt tgaagaaggc gactttgtag ctggtccttg tctatgttcc ttggaacagg   120
acgtcataga gggtgagaat cccgtgtggc gaggatccca gttatttgta aagtgctttc   180
gacgagtcga gttgtttggg aatgcagctc taagtgggtg gtaaattcca tctaaagcta   240
aatattggcg agagaccgat agcgaacaag tacagtgatg gaaagatgaa aagaactttg   300
aaaagagagt gaaaaagtac gtgaaattgt tgaagggaa gggcatttga tcagacatgg   360
cgtttgcttc ggctttcgct gggccagcat cagttttagc ggttggataa atcctcggga   420
atgtggctct gcttcggtag agtgttatag cccgtgggaa tacagccagc tgggactgag   480
gattgcgact tttgtcaagg atgctggcgt aatggttaaa tgccgcccgt cttgaaacac   540
ggaccaagga gtctaacgtc tatgcgagtg tttgggtgta aaacccgtac gcgtaatgaa   600
agtgaacgta ggtgagggcc cgcaagggtg catcatcgac cgatcctgat gtcttcggat   660
ggatttgagt aagagcatag ctgttgggac ccgaaagatg gtgaactatg cctgaatagg   720
gtgaagccag aggaaactct ggtggaggct cgtagcggtt actgacgtgc aaatcgatcg   780
tcgaatttgg gtatagggcg                                               800
```

METHOD FOR PRODUCING BIOETHANOL FROM DATES

INCORPORATION BY REFERENCE OF MATERIAL SUBMITTED IN COMPUTER READABLE FORM

The Applicant hereby incorporates by reference the sequence listing contained in the ASCII text file titled 32087_09_sequence_listing_ST25.txt, created Mar. 14, 2019, and having 17 KB of data.

BACKGROUND

1. Field

The disclosure of the present patent application relates to biofuels, and particularly to a method for producing bioethanol from dates.

2. Description of the Related Art

Bioethanol is ethyl alcohol produced from biological sources. Bioethanol can be used as fuel, or as a fuel additive for gasoline. Bioethanol is commonly made from biomass such as corn or sugarcane. Other common sources for bioethanol include potato, cassava, barley, wheat, and hemp.

Bioethanol is manufactured from grains by milling the grains into meal, mixing the meal with water and alpha-amylase and liquefying the resulting mash. This step is followed by saccharification with a secondary enzyme to convert the liquefied starch to fermentable sugars, fermentation with yeast, distillation of the fermented mash to concentrate the alcohol, and dehydration to remove any remaining water, resulting in anhydrous ethanol.

The traditional approach to manufacturing bioethanol suffers from a number of drawbacks. The use of grains to produce bioethanol could contribute to rising food prices. The process of producing ethanol from grain is highly inefficient, requiring many wasteful steps, including hydrolysis of starch by addition of enzymes and acids.

Thus, a method for producing bioethanol from dates solving the aforementioned problems is desired.

SUMMARY

The method for producing bioethanol from dates includes manufacturing a suitable substrate for bioethanol from dates and fermenting the date substrate to produce bioethanol. In one embodiment, the date substrate can be produced by de-pitting date fruits, heating the flesh with water to produce a mixture, filter pressing the mixture to produce a juice, and concentrating the juice by vacuum drying to produce a date substrate. The date substrate may then be fermented in either a batch or a fed-batch culture. In the batch process, the entire volume of substrate may be added to a bioreactor along with a yeast inoculum and fermentation may be conducted at either 30° C. or 40° C., depending upon the strain of yeast used as the inoculum. In the fed-batch process, the substrate may be fed gradually into the bioreactor containing the yeast inoculum at a constant feeding rate and fermentation may be conducted at either 30° C. or 40° C., depending upon the strain of yeast used as the inoculum.

In an alternative embodiment, the date substrate may be date extract.

These and other features of the present disclosure will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
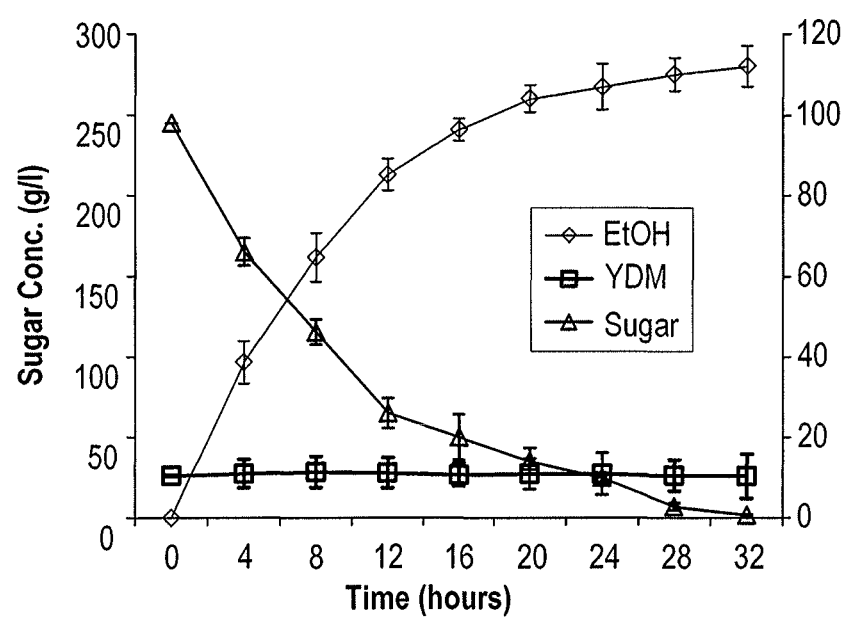
FIG. 1: depicts a graph of ethanol production from date extract in batch using a commercial strain of S. cerevisiae.

As used herein, the term "about," when used to modify a quantity, means within 10% of the modified quantity.

A method for producing bioethanol from dates includes manufacturing a suitable substrate from dates and fermenting the date substrate to produce bioethanol. The date substrate may be "Dips," a date substrate produced by de-pitting date fruits, heating the flesh with water to produce a mixture, filter pressing the mixture to produce a juice, and concentrating the juice by vacuum drying to produce a date substrate. The date substrate may then be fermented in either a batch or a fed-batch culture. In the batch process, the entire volume of substrate may be added to a bioreactor along with a yeast inoculum and fermentation can be conducted at about 30° C. or about 40° C., depending upon the strain of yeast used as the inoculum. In the fed-batch process, the substrate may be gradually fed into the bioreactor containing the yeast inoculum at a constant feeding rate and fermentation can be conducted at about 30° C. or about 40° C., depending upon the strain of yeast used as the inoculum.

In an embodiment, the de-pitted date fruits may be heated with an equal volume of water at about 80° C. for about 30 minutes to produce the mixture.

The filter pressing step is particularly useful to remove large impurities and insoluble matter. In an embodiment, the juice may be further purified to provide a clear liquid by micro filtration using a sheet filter system prior to the concentration step. This embodiment is particularly suited to applications where it is desirable to remove smaller impurities from the juice.

In an embodiment, the vacuum drying step may involve concentrating the juice or the clear extract to about 75° Brix at a low temperature, such as about 80° C.

In an alternative embodiment, the date substrate may be date extract. The date extract may be produced by mixing date fruits 1:4 (w/w) with water, boiling the water for about 60-90 minutes, and filtering the mixture to produce a date extract. The date extract may then be sterilized in an autoclave at about 121° C. for about 30 minutes.

In an embodiment, the date fruits may be waste date fruits, e.g., date fruits not fit for consumption. In a further embodiment the waste date fruits include one or more of the Ruzeiz, Shunaizi, and Shahal varieties of dates. In a further embodiment, the waste date fruits may be waste date fruits harvested in Saudi Arabia. In an embodiment of the present methods, one ton of waste date fruits with an average of 70% sugar content can provide an extract having about 600 kg sugars, which can provide about 300 kg to about 600 kg, e.g., 400 kg, of ethanol.

In an embodiment, the fermentation may be conducted using a yeast such as S. cerevisiae, K. marxianus, or the like. In a further embodiment, the fermentation may be conducted at about 30° C. using a yeast strain such as S. cerevisiae, K. marxianus, S. cerevisiae NCYC 432, K. marxianus NCYC 179, or the like. In an alternative embodiment, the fermentation may be conducted at about 40° C. using a thermophilic yeast strain. The thermophilic yeast strain may be a thermophilic strain of K. marxianus, e.g., a strain isolated from local habitats in Alahsa, Saudi Arabia. The thermophilic K. marxianus strain may include at least one of the DNA sequences of SEQ ID NOs: 5-16. The thermophilic yeast strain may be K. marxianus HH 5. The K. marxianus HH 5 strain may include the DNA sequences of SEQ ID NO: 5 and/or SEQ ID NO: 6.

In an embodiment, the fermentation may be conducted using date substrate with a starting sugar concentration ranging from about 20% to about 25%.

The following examples illustrate the present teachings:

Example 1

Chemical Analysis of Dips

As discussed above, Dips were manufactured by de-pitting date fruits and heating the flesh with an equal amount of water at 80° C. for 30 minutes to produce a mixture; filter pressing the mixture to produce a juice; micro filtering the juice to a clear liquid using a sheet filter system; and concentrating the clear extract to 75 Brix at low temperature (80° C.) by vacuum drying. Chemical analysis of Dips manufactured according to this process demonstrated that the Dips included the following nutrients: about 80% sugars, mainly in form of fructose (41%) and glucose (38%), and a small amount of sucrose (%); about 2% crude protein; 1.1 g/kg phosphorus; 14.9 g/kg potassium; 0.8 g/kg magnesium; 240 ppm pantothenic acid; and 2.7 ppm biotin. (See Table 1) Therefore, Dips used as carbon and energy source in alcoholic fermentation would be expected to yield about 400 kg ethanol (about 500 liters).

Example 2

Chemical Analysis of Date Extracts

Waste date fruits were obtained from a date processing factory in Al Hofuf City, Saudi Arabia. They were mainly a collection from the varieties Ruzeiz, Shunaizi, and Shahal. Extraction of syrup from the fruits was performed as follows: 1:4 (w/w) fruit: water, boiling for about 60-90 minutes and filtration. The resulting substrate was sterilized in 5-liter bottles by autoclaving at 121° C. for 30 minutes. The sterilized substrate contained about 30% sugar.

The chemical composition of the date sterilized substrate was assessed, including determining protein concentration using the Kjeldhal method, M-Inositol concentration using and biotin and pantothenic acid concentration according to the vitaFast vitamin testing method, using an ELISA Reader (Multiskan EX Model No. 355, Thermolabsystem-Finlan). M-Inositol was determined with High Performance Liquid Chromatography (HPLC) using a Shimadzu Japan Model 2003, equipped with a RID 10A refractive index detector, CLC NH2 6×150 column, LC 10ATP pump, and CTO 10AC VP oven. The mobile phase was 83% CH3CN:17% water (v/v), flow rate 1 ml/min., column pressure 200 KgF/cm². Ethanol and sugar (glucose, fructose, and sucrose) concentrations were determined using the enzymatic UV method (Boehringer Mannheim). Mineral concentrations (Mg, P, K, and S) were determined using the atomic absorption method. The average chemical composition of the date sterilized substrate is shown in Table 1.

TABLE 1

Date Extract Nutrient Analysis

| Chemicals | Content |
|---|---|
| Total sugars (% w/w) | |
| Fruit | 68-72 |
| Thin Extract | 25-30 |
| Extracted Fruit | 10.2-10.8 |
| pH | 4.3-4.5 |
| Crude protein (% w/w) | 2.0-2.5 |
| Magnesium (g/kg) | 0.5-0.9 |
| Potassium (g/kg) | 14.0-16.0 |
| Phosphorous (g/kg) $PO_4$ or P | 1.0-1.4 |
| Pantothenic acid (ppm) | 200-240 |
| Biotin (ppm) | 2.0-3.0 |
| m-Inositol (ppm) | traces |

The date substrate contained all nutrients needed for a small amount of yeast growth (See Table 1) and no addition of mineral medium was needed. The fruits contained 68-72% (w/w) sugars on wet basis and the thin extract contained 25-30% (w/w) sugars on wet basis, with 10.2-10.8% (w/w) sugar content remaining in the extracted fruit. Hence, the efficiency of our extraction system was about 85%. As a result, a ton of waste date fruits with an average of 70% sugar content can be expected to produce a date substrate containing about 600 kg sugars, which in turn would be expected to produce about 300 kg bioethanol. If the efficiency of extraction is raised, such as by using high quality equipment, the yield of bioethanol would be predicted to increase to more than 315 kg from a ton of waste date fruits. If the sugar content of the fruits is increased, this would also be predicted to increase the resulting bioethanol yield.

Example 3

Identification of Thermotolerant Yeasts

A screening program was carried out to search for thermotolerant yeasts from the local habitat in Saudi Arabia that can be used for ethanol production. Samples of microbially spoiled fruits, especially date fruits, were collected from Hofuf markets and farms. Yeasts involved in spoilage were isolated by inoculation on PDA dishes and incubation at 35-50° C. for 2-3 days. Colonies of different forms were picked, purified by successive streaking on PDA dishes, and the pure cultures were kept in the refrigerator in PDA tubes for identification.

The strains were cultivated on Malt Extract Agar for 3 days in the dark at 25° C. DNA was isolated using the MoBio-UltraClean™ Microbial DNA Isolation Kit according to the manufacturer's instructions. Fragments including the 26S ribosomal RNA gene, Large Subunit D1 and D2 region (LSU) were amplified using the primers LR0R: ACCCGCTGAACTTAAGC (SEQ ID NO: 1) and LR5: TCCTGAGGGAAACTTCG (SEQ ID NO: 2). Fragments including the Internal Transcribed Spacer 1 and 2 and the 5.8S gene (ITS) were amplified using the primers LS266: GCATTCCCAAACAACTCGACTC (SEQ ID NO: 3) and V9G TTACGTCCCTGCCCTTTGTA (SEQ ID NO: 4). The PCR fragments were sequenced with the ABI Prism® Big Dye™ Terminator v. 3.0 Ready Reaction Cycle sequencing Kit. Samples were analyzed on an ABI PRISM 3730 Genetic Analyzer and contigs were assembled using the forward and reverse sequences with the SeqMan program from the LaserGene package. The sequence was compared in a large yeast database of CBS-KNAW Fungal Biodiversity Centre with sequences of known strains.

Twenty two isolates that showed good growth at 45° C. were obtained from the screening program. Twelve of these isolates grew at 50° C., and hence were regarded as thermophilic. Preliminary identification tests were carried out on the 12 thermophilic isolates, including morphological examination of the yeast colonies grown on PDA, microscopic examination of the cell form, and ability to ferment glucose. The outcome of these tests indicated that the 12 thermophilic isolates belonged to at least to 3 different genera. Molecular identification of these 12 thermophilic isolates by DNA sequencing was carried out and the results are shown in Table 2. The isolates belonged to three genera and species, namely *Kluyveromyces marxianus* (6 isolates), *Clavispora lusitaniae* (5 isolates and *Wickerhamomyces anomalus* (1 isolate). *C. lusitaniae* is an opportunistic pathogen, hence it was not considered for ethanol production. Preliminary tests showed that *W. anomalus* was not a good ethanol producer. However, promising preliminary results for ethanol production were obtained for the strains of *K. marxianus*, and the best of these isolates was *K. marxianus* 05-1 or "HH5."

The isolates belonging to the same species had different genetic sequences at the tested loci, indicating that they are different strains of the species. The sequence of the 26S ribosomal RNA gene, Large Subunit D1 and D2 region (LSU) of the *K. marxianus* 05-1 isolate includes SEQ ID. NO. 6. The sequence of the 26S ribosomal RNA gene, Large Subunit D1 and D2 region (LSU) of the *K. marxianus* 12-1 isolate includes SEQ ID. NO. 8. The sequence of the 26S ribosomal RNA gene, Large Subunit D1 and D2 region (LSU) of the *K. marxianus* 14G-1 isolate includes SEQ ID. NO. 10. The sequence of the 26S ribosomal RNA gene, Large Subunit D1 and D2 region (LSU) of the *K. marxianus* 14W-1 isolate includes SEQ ID. NO. 12. The sequence of the 26S ribosomal RNA gene, Large Subunit D1 and D2 region (LSU) of the *K. marxianus* 23-1 isolate includes SEQ ID. NO. 14. The sequence of the 26S ribosomal RNA gene, Large Subunit D1 and D2 region (LSU) of the *K. marxianus* 25-1 isolate includes SEQ ID. NO. 16. The sequence of the Internal Transcribed Spacer 1 and 2 and the 5.8 gene (ITS) of the *K. marxianus* 05-1 isolate includes SEQ ID. NO. 5. The sequence of the Internal Transcribed Spacer 1 and 2 and the 5.8S gene (ITS) of the *K. marxianus* 12-1 isolate includes SEQ ID. NO. 7. The sequence of the Internal Transcribed Spacer 1 and 2 and the 5.8S gene (ITS) of the *K. marxianus* 14G-1 isolate includes SEQ ID. NO. 9. The sequence of the Internal Transcribed Spacer 1 and 2 and the 5.8S gene (ITS) of the *K. marxianus* 14W-1 isolate includes SEQ ID. NO. 11. The sequence of the Internal Transcribed Spacer 1 and 2 and the 5.8S gene (ITS) of the *K. marxianus* 23-1 isolate includes SEQ ID. NO. 13. The sequence of the Internal Transcribed Spacer 1 and 2 and the 5.8S gene (ITS) of the *K. marxianus* 25-1 isolate includes SEQ ID. NO. 15.

TABLE 2

Identification of Yeast Isolates Using Morphological and Molecular Characteristics

| Strain | Name |
|---|---|
| 05-1 | *Kluyveromyces marxianus* (E. C. Hansen) Van der Walt (named *K. marxianus* HH5) |
| 12-1 | *Kluyveromyces marxianus* (E. C. Hansen) Van der Walt |
| 14G-1 | *Kluyveromyces marxianus* (E. C. Hansen) Van der Walt |
| 14W-1 | *Kluyveromyces marxianus* (E. C. Hansen) Van der Walt |

TABLE 2-continued

Identification of Yeast Isolates Using Morphological and Molecular Characteristics

| Strain | Name |
|---|---|
| 23-1 | *Kluyveromyces marxianus* (E. C. Hansen) Van der Walt |
| 25-1 | *Kluyveromyces marxianus* (E. C. Hansen) Van der Walt |
| 15-2 | *Clavispora lusitaniae* Rodr. Mir. |
| 26-2 | *Clavispora lusitaniae* Rodr. Mir. |
| 28-2 | *Clavispora lusitaniae* Rodr. Mir. |
| 45-2 | *Clavispora lusitaniae* Rodr. Mir. |
| 50-2 | *Clavispora lusitaniae* Rodr. Mir. |
| 48-2 | *Wickerhamomyces anomalus* (E. C. Hansen) Kurtzman, Robnett & Basehoar-Powers |

Example 4

Fermentation Experimental Design

The yeast strains were first propagated in shake flasks and then in a bioreactor containing suitable medium, harvested by filtration to a cake and kept in the refrigerator to be used as inocula.

Fermentation experiments were done in batch and fed-batch cultures using shake flasks, a BioFlo 110 bioreactor (New Brunswick Scientific) with 10 liter working volume and an Applikon autoclavable Bioreactor system (Applikon Biotechnology, the Netherlands) with one liter working volume. In the batch process, the whole substrate was added to the bioreactor at the beginning of fermentation and the process continued to its end. In the fed-batch process the substrate was fed to the fermenter at constant feeding rates. Fermentations using the commercial baker's yeast, *S. cerevisiae* NCYC 432, and *K. marxianus* NCYC 179 were at 30° C., while fermentation using the thermophilic yeast *K. marxianus* HH 5 (isolated by the present inventors) was at 40° C. Samples were taken from the bioreactor every 2-4 hours and the concentrations of ethanol, sugars and yeast dry matter were determined.

A 3×4×2 (three variables) factorial experimental design was employed with three types of substrates (date extract, molasses, and a mixture of 1:1 date extract/molasses), 4 production organisms (local and imported) and two fermentation processes (batch and fed-batch) (See Table 3). A randomized block design was chosen to run the experiment. A collection of waste date fruits and 2 fermentation temperatures (30 and 40° C.) were chosen based on information from the literature. All of the above parameters were used as useful means for modeling and optimizing small-scale operations. Variables measured in this study included yield of ethanol on substrate (g ethanol/g sugar), and the concentrations (g/l) of ethanol, sugars, and yeast biomass.

TABLE 3

Experimental Design

| Independent Variable | Factor | | |
|---|---|---|---|
| Substrate | 100% Dips | 100% Molasses | 1:1 Dips/Molasses |
| Production Organism | Local isolate (one strain) | Imported strains (three strains) | |
| Production process | Batch | Fed-Batch | |

Ethanol and sugar (glucose, fructose, and sucrose) concentrations were determined using the enzymatic UV method (Boehringer Mannheim). Yeast biomass concentration was determined by centrifugation of 5 ml broth at 2000 rpm for 5 minutes in dry centrifugal tube, and overnight drying at 105° C.

The yeasts used were *S. cerevisiae* NCYC 431, *Kluyveromyces marxianus* NCYC 179, a commercial baker's yeast strain of the species *S. cerevisiae* purchased from the local market, and *K. marxianus* HH 5 (isolated by the present inventors). Batch and fed-batch fermentation processes were used at different final sugar concentrations. For comparison, substrates of pure molasses and a 1:1 mixture of date extract and molasses were also used for production. The fermentation experiments were done using shake flasks, a BioFlo 110 bioreactor (New Brunswick Scientific) with 10 liter working volume and an Applikon autoclavable Bioreactor system (Applikon Biotechnology, the Netherlands) with one liter working volume.

Date substrate was extracted as described in Example 1. The fruits used were waste fruits collected from a date processing factory in Hofuf City, mainly made of the varieties Ruzeiz, Shunaizi, and Shahal. Because yeast growth during ethanol production is normally minimal, sugars in the production substrate are mainly converted to ethanol and no significant amount of yeast biomass is formed.

Four yeast strains were used for production including a commercial baker's yeast strain of the species *S. cerevisiae*, *K. marxianus* NCYC 179, *S. cerevisiae* NCYC 431 and the strain *K. marxianus* HH 5 (isolated by the present inventors). Production was in batch and fed-batch cultures at fermentation temperatures of 30 and 40° C. Three substrates were used, namely pure date extract, pure molasses and a mixture of date extract and molasses at 1:1 ratio, with sugar concentrations of 20 to 25%. The results, all of which were averages of three runs, are presented in FIGS. 1 to 26.

Example 5

Fermentation Testing with Commercial *S. cerevisiae*

The strain of the baker's yeast from the species *S. cerevisiae* was used for ethanol production in batch processes at fermentation temperatures of 30° C. on substrates of pure date extract, pure molasses and a 1:1 mixture of date extract and molasses. Samples were taken every 4 hours and the concentrations of ethanol, sugar and yeast dry matter were measured. The results are shown in FIGS. 1-6.

Figure 2:
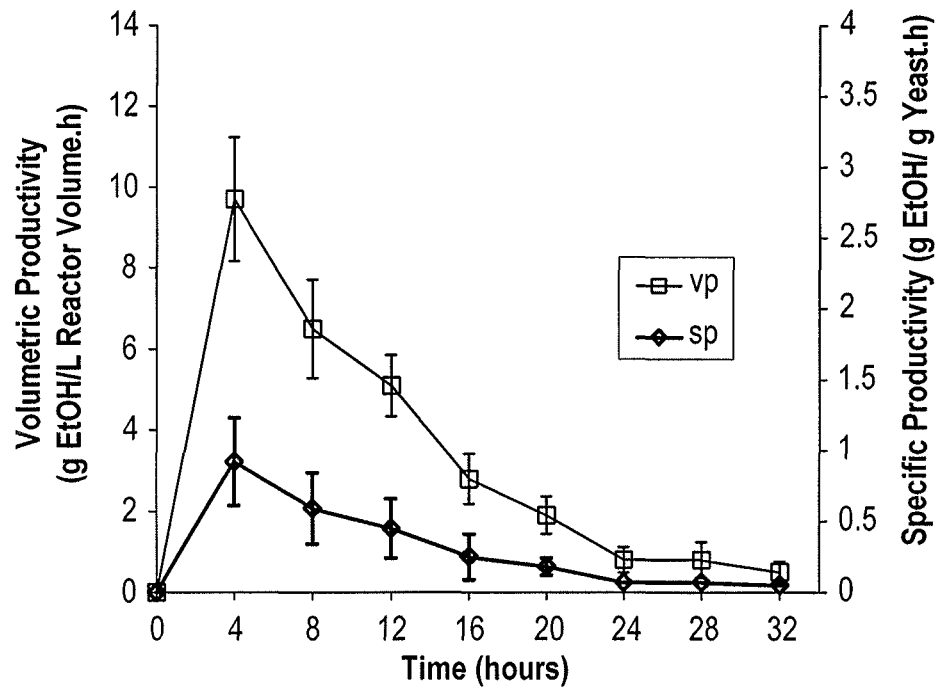
FIG. 2: depicts a graph of specific and volumetric productivities of ethanol from date extract in batch using a commercial strain of S. cerevisiae.

Ethanol production from date extract continued at a relatively high rate during the first 12 hours of fermentation, the concentration increased steadily during this period to reach 85.2 g/l (FIG. 1). After that, the production rate decreased towards the end of the fermentation period of 32 hours and the final ethanol concentration reached was 112.1 g/l (11.2% w/v). The course of ethanol productivity is illustrated in FIG. 2. The specific and volumetric productivities were relatively high during the first 12 hours of fermentation, after which they decreased steadily to reach very low values towards the end of the fermentation period. During the first 4 hours of fermentation the specific productivity was 0.92 g ethanol per g yeast per hour (g/g·h) and the volumetric productivity was 9.7 g ethanol per liter reactor volume per hour (g/l·h). At the end of fermentation after 32 hours, the specific productivity decreased to 0.05 g/g·h and the volumetric productivity decreased to 0.5 g/l·h. It is apparent that increased ethanol concentration in the fermentation medium was inhibitory to production, and the maximum amount produced and tolerated by the yeast was 11.2% (w/v). The specific productivity is mainly a measure of the efficiency of the yeast in ethanol production and the volumetric productivity is mainly a measure of the efficiency of the bioreactor system. The overall yield of ethanol on sugar was 91.5% of the theoretical. There was no significant yeast growth during fermentation, as yeast biomass concentration remained almost constant during the whole period of fermentation (FIG. 1). The sugar was almost completely consumed, with only traces remaining at the end of the fermentation period (FIG. 1). Generally, the values obtained for the yield of ethanol on sugar and for the specific and volumetric productivities are comparable to values reported for different organisms and substrates.

Figure 3:
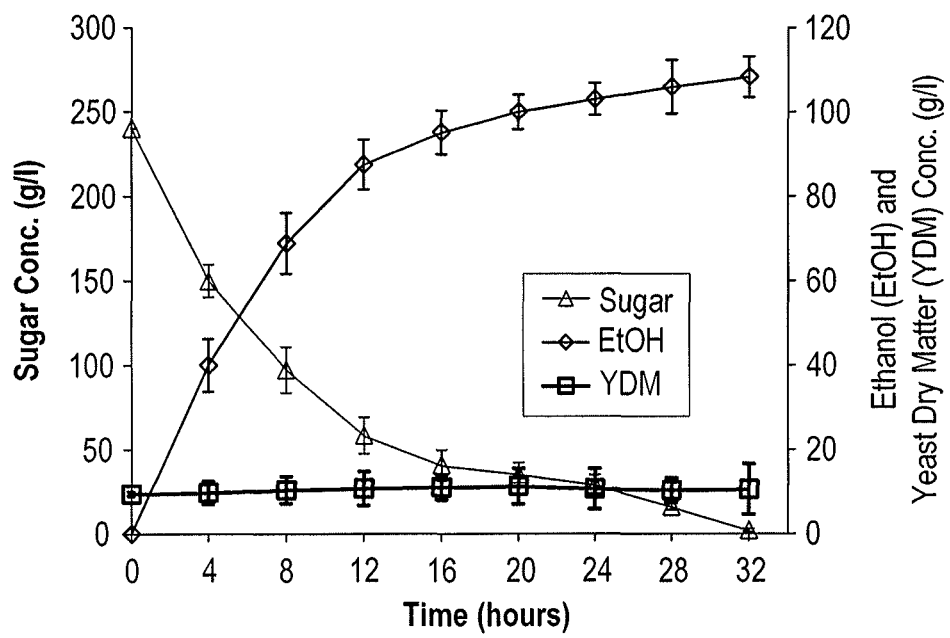
FIG. 3: depicts a graph of ethanol production from molasses in batch using a commercial strain of S. cerevisiae.
Figure 4:
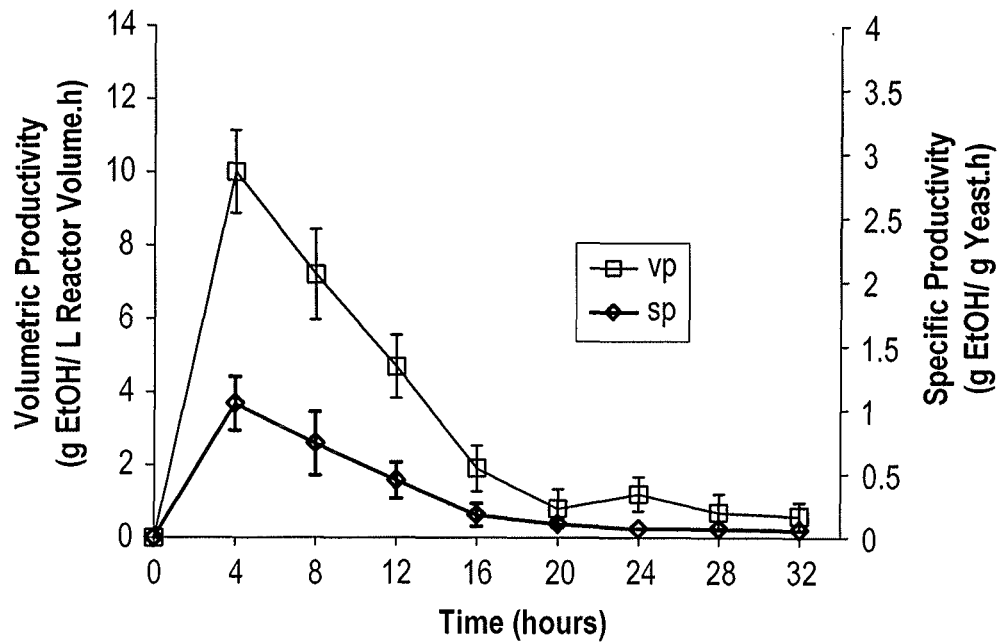
FIG. 4: depicts a graph of specific and volumetric productivities of ethanol from molasses in batch using a commercial strain of S. cerevisiae.
Figure 5:
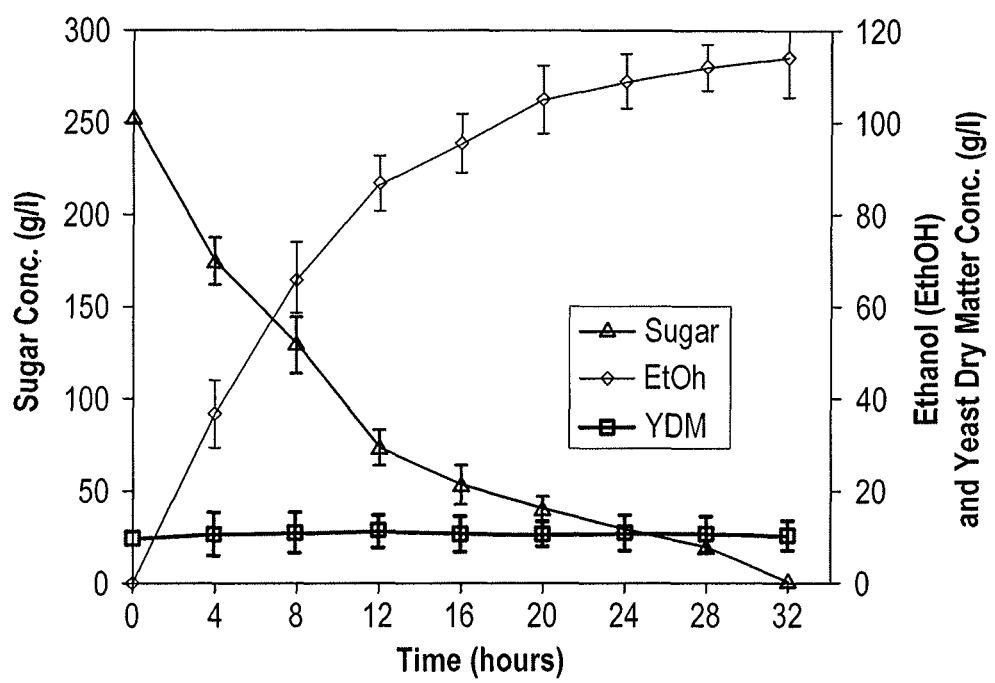
FIG. 5: depicts a graph of ethanol production from date extract and molasses (1:1) in batch using a commercial strain of S. cerevisiae.
Figure 6:
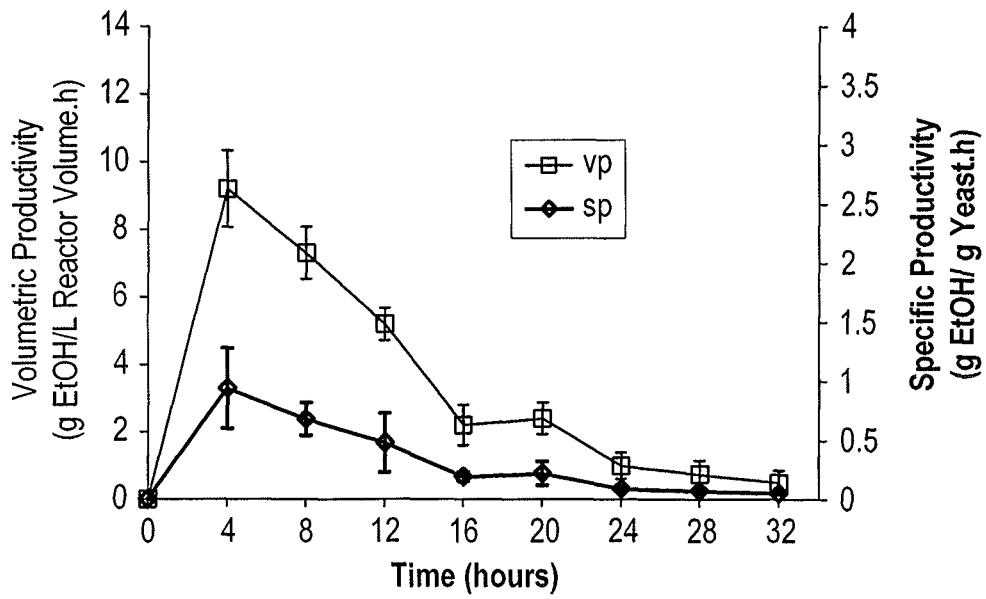
FIG. 6: depicts a graph of specific and volumetric productivities of ethanol from date extract and molasses (1:1) in batch using a commercial strain of S. cerevisiae.

Substrates of pure molasses and a 1:1 mixture of date extract and molasses were used for ethanol production under conditions similar to those of the pure date extract. The results of molasses fermentation are presented in FIGS. 3 and 4. These results were quite similar to those of pure date extract (FIG. 3). Most production occurred in the first 12 hours of fermentation, after which production rate started to slow down and the final ethanol concentration reached was 108.4 g/l (10.8% w/v). The specific and volumetric productivities were also comparable to those of the pure date extract (FIG. 4). The specific productivity after 4 hours of fermentation was 1.05 g/g·h and the volumetric was 10.0 g/l·h, and both decreased to 0.06 g/g·h and 0.6 g/l·h at the end of fermentation, respectively. The yield of ethanol on sugar was 90.3% of the theoretical, which was a little lower than that of pure date extract, but statistical analysis showed that the difference was not significant. No significant yeast growth occurred and the sugar provided was almost completely utilized with only traces remaining at the end of the fermentation period (FIG. 3). A similar result was obtained using the 1:1 date extract and molasses mixture (FIGS. 5 and 6). The final ethanol concentration was 114.0 g/l (11.4% w/v), the specific and volumetric productivities 0.94 g/g·h and 9.2 g/l·h after 4 hours and 0.05 g/g·h and 0.5 g/l·h at the end of fermentation, respectively. The yield of ethanol on sugar was 90.1% of the theoretical and was not significantly different from the yields obtained for the other two substrates as statistical analysis showed. Again, no significant yeast growth occurred and the sugar was largely consumed with very small amount remaining at the end of fermentation (FIG. 5). It can therefore be said that this commercial yeast strain of the species *S. cerevisiae* can produce ethanol from date extract in efficiency comparable to that of the reference substrate molasses. That is to say that date extract substrate is quite suitable for ethanol production.

Example 6

Fermentation Testing with *K. marxianus* NCYC 179

Figure 7:
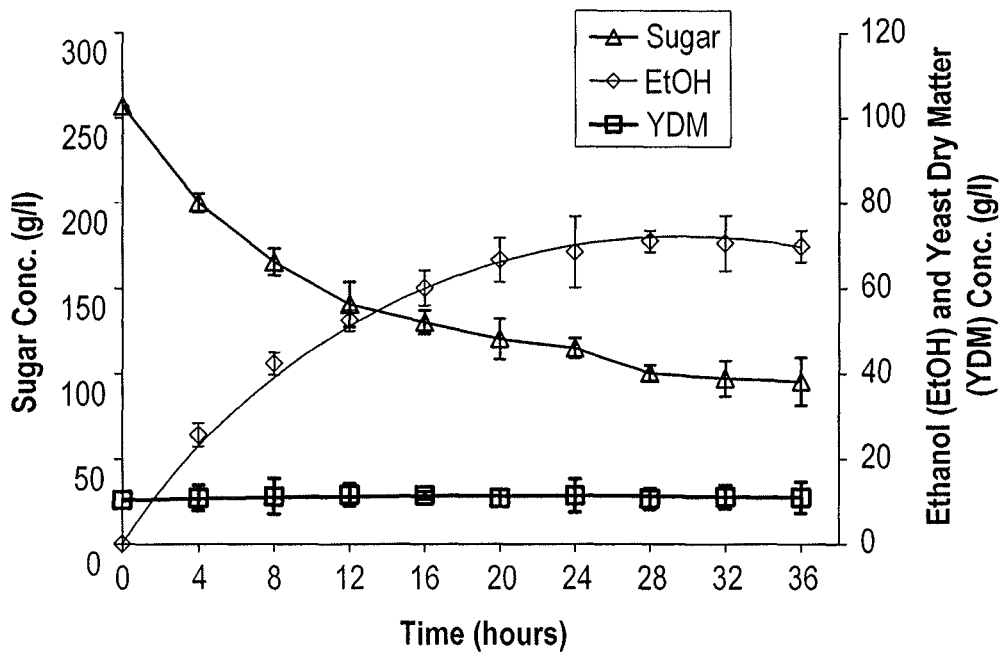
FIG. 7: depicts a graph of ethanol production from date extract in batch using K. marxianus NCYC 179.
Figure 8:
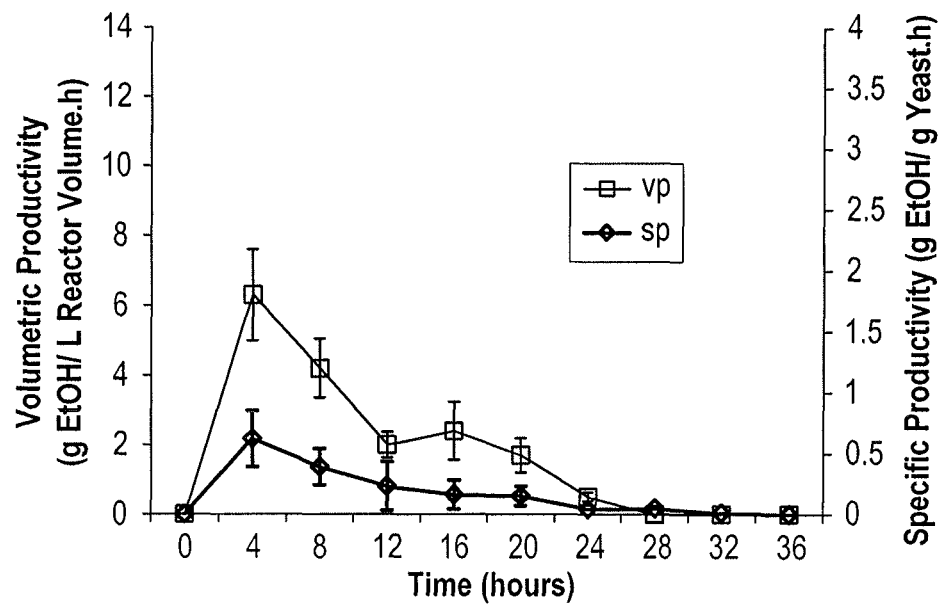
FIG. 8: depicts a graph of specific and volumetric productivities of ethanol from date extract in batch using the yeast K. marxianus NCYC 179.

The strain *Kluyveromyces marxianus* NCYC 179 was used for ethanol production in batch processes at fermentation temperatures of 30° C. on a substrate of pure date extract. Samples were taken every 4 hours and the concentrations of ethanol, sugar and yeast dry matter were measured. The results are shown in FIGS. 7 and 8.

The performance of this yeast was generally weak. The concentration of ethanol after the first 4 hours of fermentation was only 25.6 g/l, which was much lower than the concentration reached from the commercial baker's yeast reported above (FIG. 7). The maximum ethanol concentration was 71 g/l (7.1% w/v); it was reached after 28 hours of fermentation. The specific and volumetric productivities were also much lower than the values reported above for the commercial baker's yeast. They were 0.62 g/g·h for the specific productivity and 6.3 for the volumetric productivity after 4 hours of fermentation and 0.05 g/g·h and zero after 28 hours, respectively (FIG. 8). No increase in ethanol concentration occurred when fermentation was continued to 36 hours. The yield was only 54.9% of the theoretical, which was much lower than that obtained from the commercial yeast. The sugar was not fully utilized, and 95.6 g/l remained unconsumed in the fermentation broth. This suggests that this yeast cannot produce and tolerate more than 7% w/v ethanol. For this reason, further experiments were not performed with this yeast strain.

Example 7

Fermentation Testing with *S. cerevisiae* NCYC 431

The yeast strain *S. cerevisiae* NCYC 431 was used for ethanol production in batch processes at fermentation temperatures of 30° C. on substrates of pure date extract, pure molasses and a 1:1 mixture of date extract and molasses. Samples were taken every 4 hours and the concentrations of ethanol, sugar and yeast dry matter were determined. The results are shown in FIGS. 9-14.

Figure 9:
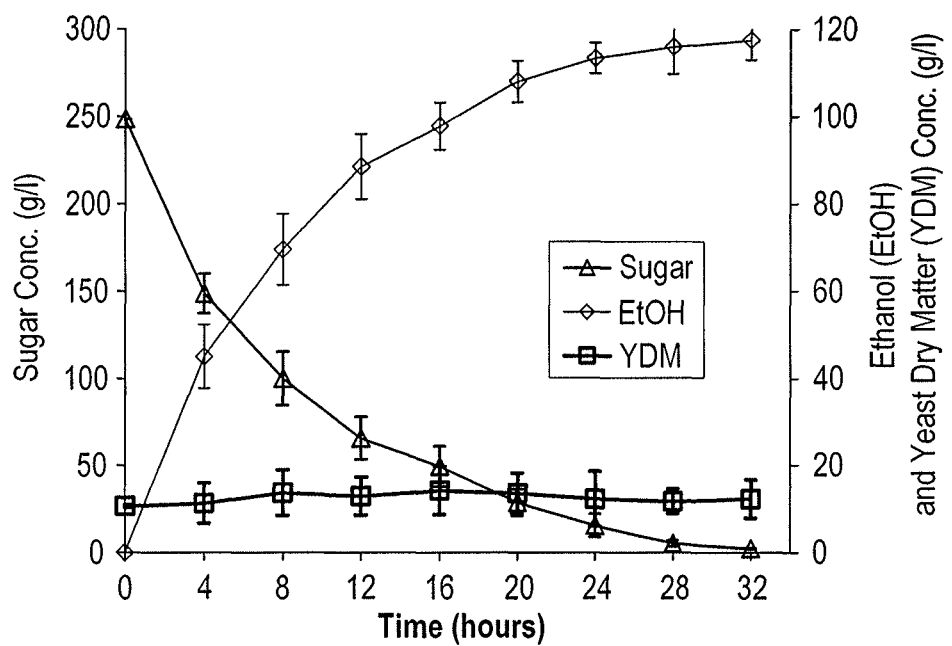
FIG. 9: depicts a graph of ethanol production from date extract in batch using the yeast S. cerevisiae NCYC 431.
Figure 10:
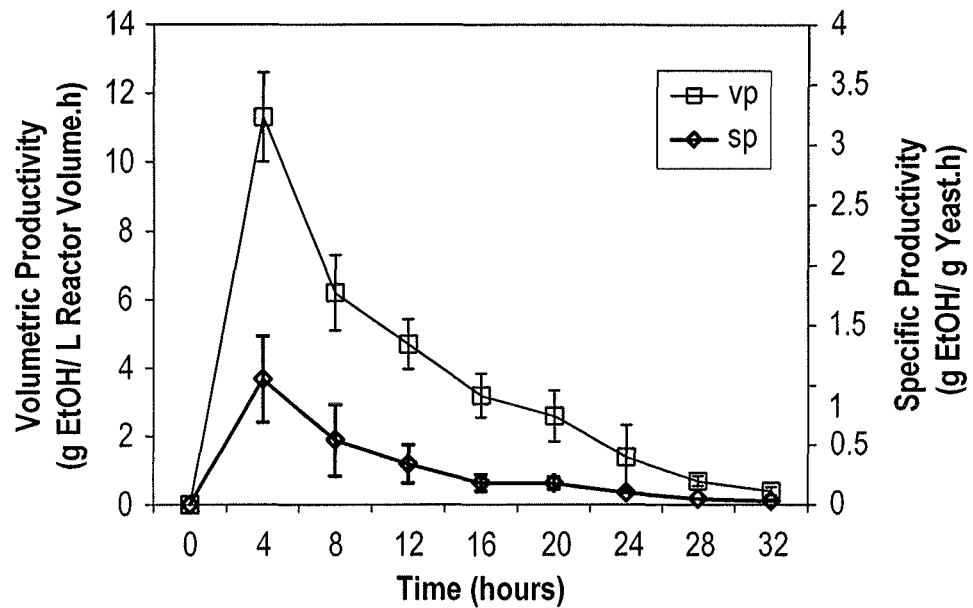
FIG. 10: depicts a graph of the specific and volumetric productivities of ethanol from date extract in batch using the yeast S. cerevisiae NCYC 431.

Ethanol production from date extract substrate started at a relatively high rate compared to the other yeast strains discussed above. The concentration reached 45 g/l in the first 4 hours and continued to increase at a decreasing rate till it reached 117.6 g/l (11.8% w/v) at the end of fermentation of 32 hours (FIG. 9). The specific productivity started at 1.05 g/g·h in the first 4 hours and ended at 0.03 g/g·h at the end of fermentation, while the volumetric productivity was 11.3 and 0.4 g/l·h after 4 and 32 hours of fermentation, respectively (FIG. 10). The yield of ethanol on sugar was 94.6% of the theoretical, indicating that sugar was mainly converted into ethanol and no significant amounts of other metabolic products were formed. Sugar provided was consumed to traces remaining and no significant yeast growth occurred.

Figure 11:
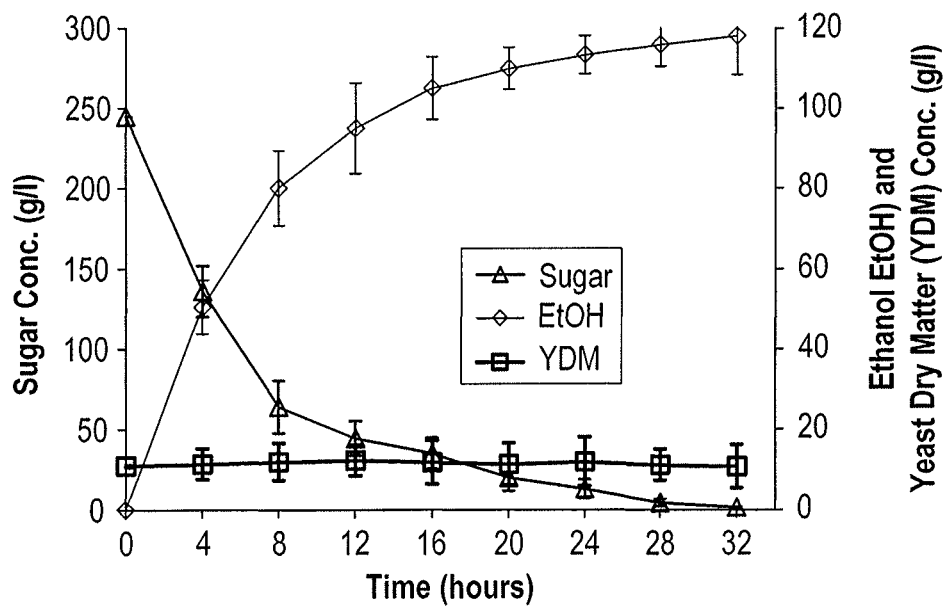
FIG. 11: depicts a graph of ethanol production from molasses in batch using the yeast S. cerevisiae NCYC 431.
Figure 12:
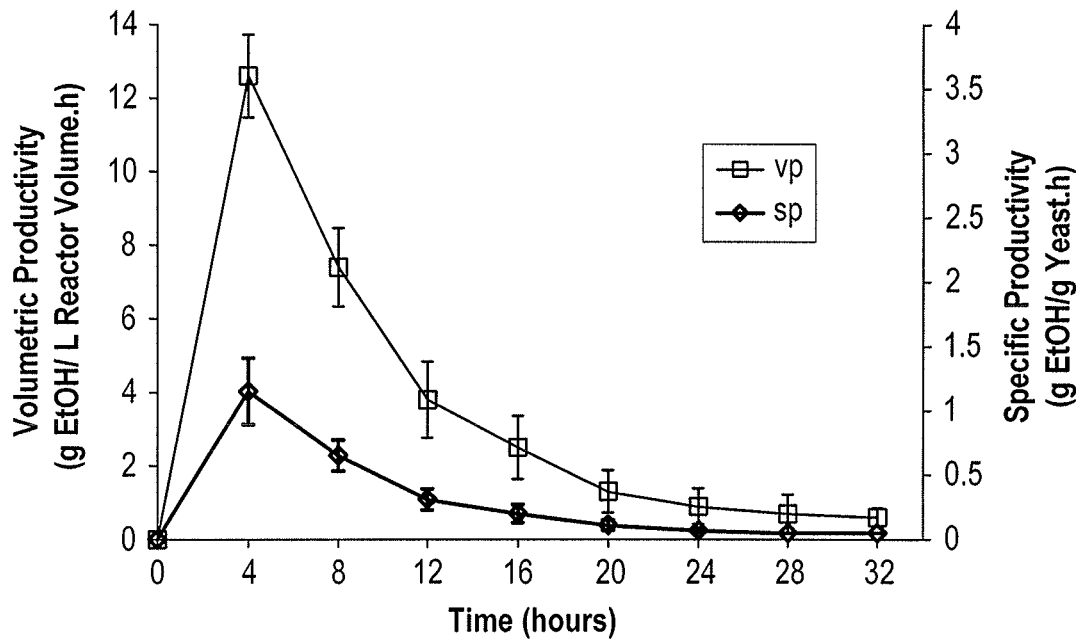
FIG. 12: depicts a graph of specific and volumetric productivities of ethanol from molasses in batch using the yeast S. cerevisiae NCYC 431.

Ethanol production from molasses substrate using the yeast strain *S. cerevisiae* NCYC 431 is presented in FIGS. 11 and 12. Ethanol concentration after 4 hours was 50.5 g/l and reached 118.2 g/l (11.8% w/v) at the end of the fermentation period of 32 hours (FIG. 11). The specific and volumetric productivities were high, starting at 1.15 g/g·h and 12.6 g/l·h in the first 4 hours, respectively and ending at 0.05 g/g·h and 0.6 g/l·h after 32 hours, respectively (FIG. 12). The yield of ethanol on sugar was also high, reaching a value of 96.6% of the theoretical, but statistical analysis showed that this result was not significantly different from the 94.6% obtained using the date extract substrate. As expected, sugar provided was almost completely consumed and no significant yeast growth occurred.

Figure 13:
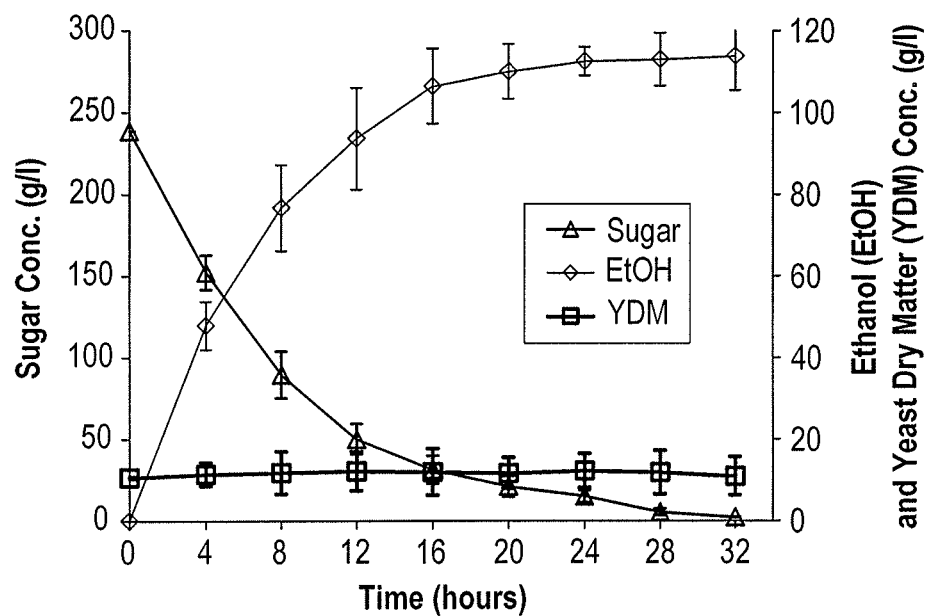
FIG. 13: depicts a graph of ethanol production from date extract and molasses (1:1) in batch using the yeast S. cerevisiae NCYC 431.
Figure 14:
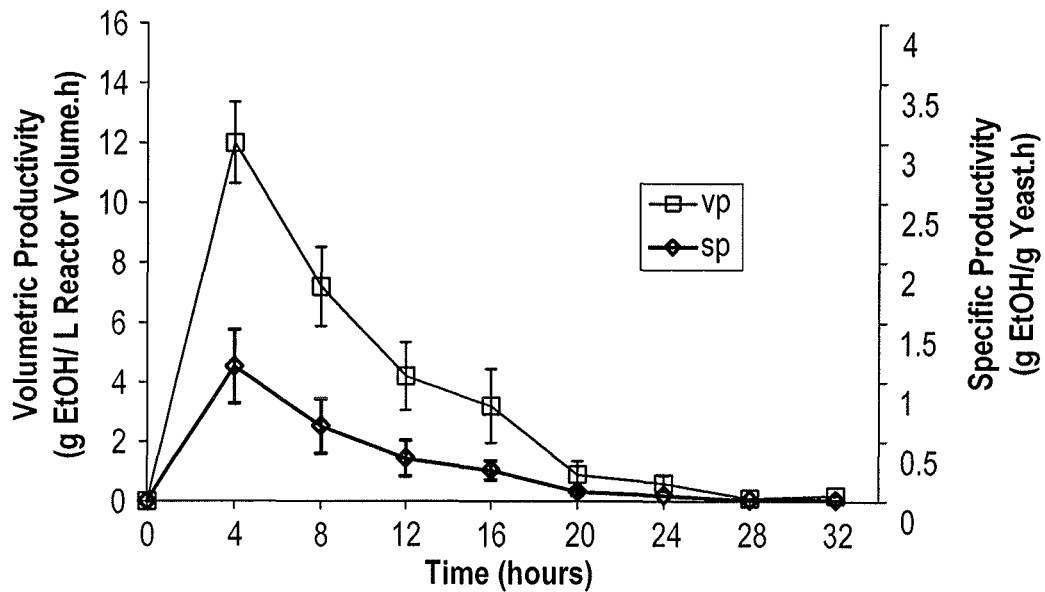
FIG. 14: depicts a graph of specific and volumetric productivities of ethanol from date extract and molasses (1:1) in batch using the yeast S. cerevisiae NCYC 431.

Ethanol production from the mixed substrate using strain *S. cerevisiae* NCYC 431 (1:1 date extract and molasses) followed a quite similar trend to the other substrates presented above (FIGS. 13 and 14). Ethanol concentration in the first 4 hours was 47.9 g/l and reached 113.8 g/l (11.4% w/v) after 32 hours of fermentation (FIG. 13). The specific and volumetric productivities were 1.13 g/g·h and 12 g/l·h after 4 hours, respectively and ended at 0.01 g/g. h and 0.2 g/l·h after 32 hours, respectively (FIG. 14). The yield of ethanol on sugar was 95.4% of the theoretical, it was the second highest, but was not significantly different from the yields of pure date extract and pure molasses.

Statistical analysis comparing the yields of ethanol on sugar obtained from the baker's yeast strain *S. cerevisiae* and from the yeast strain *S. cerevisiae* NCYC 431 showed that the yields of the latter were significantly higher. It can therefore be concluded that the yeast strain *S. cerevisiae* NCYC 431 was the best producer of ethanol from date extract substrate. Production by this yeast stain was therefore further tested in fed-batch experiments.

The strain *S. cerevisiae* NCYC 431 was used for ethanol production in a fed-batch process of fermentation to attempt to further improve its productivity. Production was at a temperature of 30° C. on substrates of pure date extract, pure molasses and a 1:1 mixture of date extract and molasses. The substrates were fed at constant rates of 200 ml/h and feeding time was 15 hours to deliver 3 liters of substrate containing about 50% sugars. Samples were taken every 2 hours and the concentrations of ethanol, sugar and yeast dry matter were measured. The results are shown in FIGS. 15-20.

Figure 15:
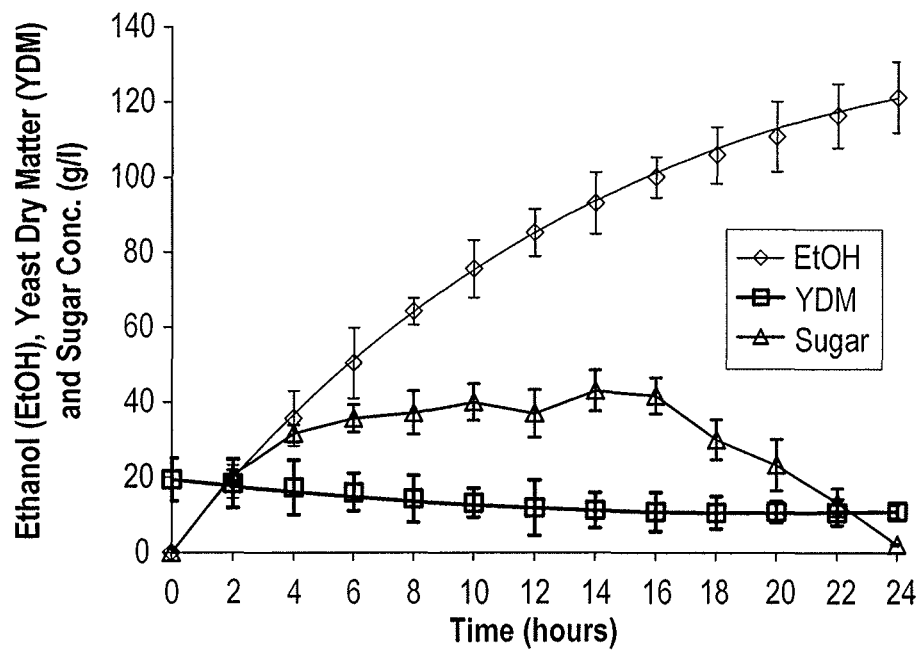
FIG. 15: depicts a graph of ethanol production from date extract in fed-batch using the yeast S. cerevisiae NCYC 431.
Figure 16:
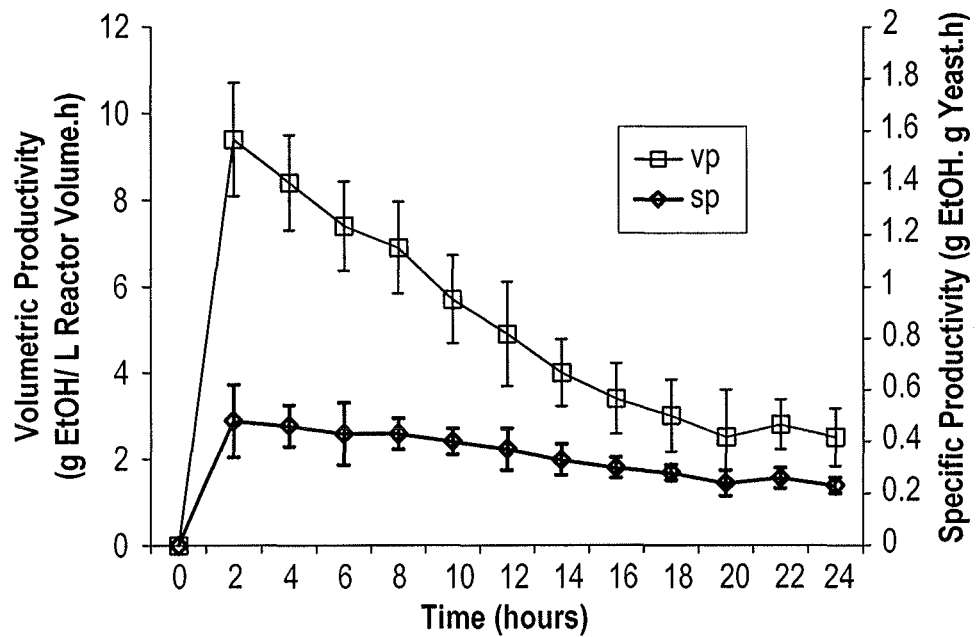
FIG. 16: depicts a graph of specific and volumetric productivities of ethanol from date extract in fed-batch using the yeast S. cerevisiae NCYC 431.

The results of the experiments using date extract as substrate are shown in FIGS. 15 and 16. Ethanol concentration reached 18.8 g/l in the first 2 hours of fermentation (FIG. 15). The concentration increased steadily and reached its maximum of 121.5 g/l (12.2% w/v) in 24 hours. The total amount of ethanol produced was not much higher than that obtained in the batch culture discussed above. The main difference was in the fermentation time, which was 24 hours in the fed-batch process compared to 32 hours in the batch process. The specific productivity decreased much slower compared to that of the batch process (FIG. 16). In the batch process the yeast was affected by the combined inhibitory effect of high concentrations of sugar and ethanol, whereas in the fed-batch process there was no inhibitory effect of sugar because its concentration remained relatively low throughout the fermentation time. Sugar concentration in the fermentation medium increased at a low rate till the end of substrate feeding after 15 hours, then decreased quickly to reach traces at the end of fermentation. No significant yeast growth occurred. The volumetric productivity in turn remained also relatively high during the whole time of fermentation indicating the absence of the combined inhibitory effect of sugar and ethanol (FIG. 16). Ethanol yield on sugar was 97.2% of the theoretical, indicating a high efficiency in converting sugar into ethanol without formation of significant amounts of other metabolic products.

Figure 17:
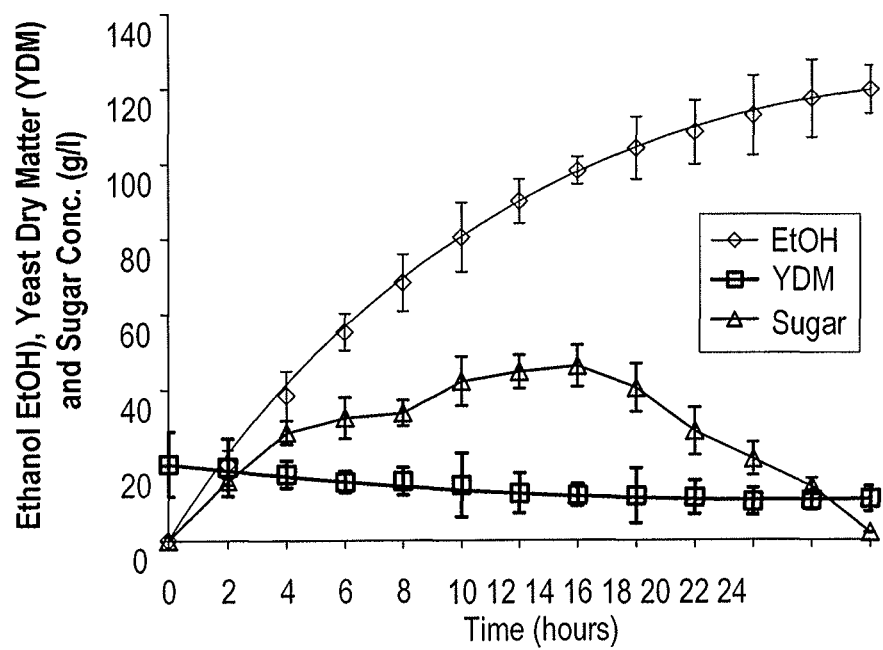
FIG. 17: depicts a graph of ethanol production from molasses in fed-batch using the yeast S. cerevisiae NCYC 431.
Figure 18:
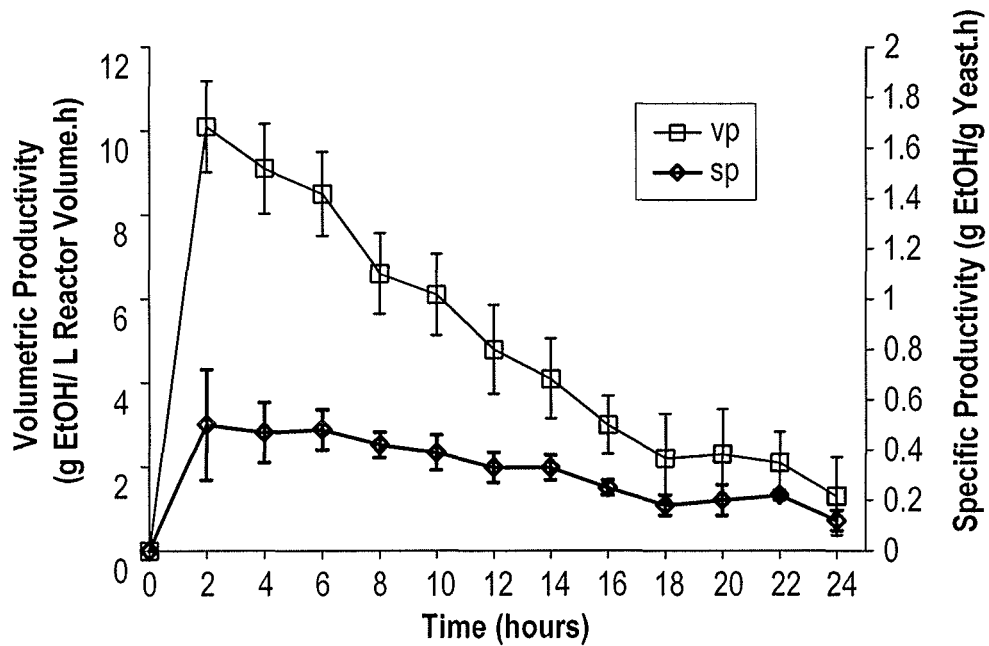
FIG. 18: depicts a graph of specific and volumetric productivities of ethanol from molasses in fed-batch using the yeast S. cerevisiae NCYC 431.

Molasses substrate gave quite similar results to date extract substrate. As can be seen in FIGS. 17 and 18, production proceeded in the same way as those of the date extract substrate. The concentration of ethanol reached 20.3 g/l in the first two hours of fermentation and continued to increase steadily to reach its Maximum of 119.9 g/l (12% w/v) after 24 hours of fermentation (FIG. 17). The specific productivity remained fairly high over the whole period of fermentation (FIG. 18). Sugar concentration increased slowly to reach 46.3 g/l towards the end of substrate feeding, and decreased quickly after that to reach very low levels (FIG. 18). No significant amount of yeast growth was noticed. The yield of ethanol on sugar was 96.4% of the theoretical, which was a little lower than that obtained from the date extract but the difference was not significant as statistical analysis revealed.

Figure 19:
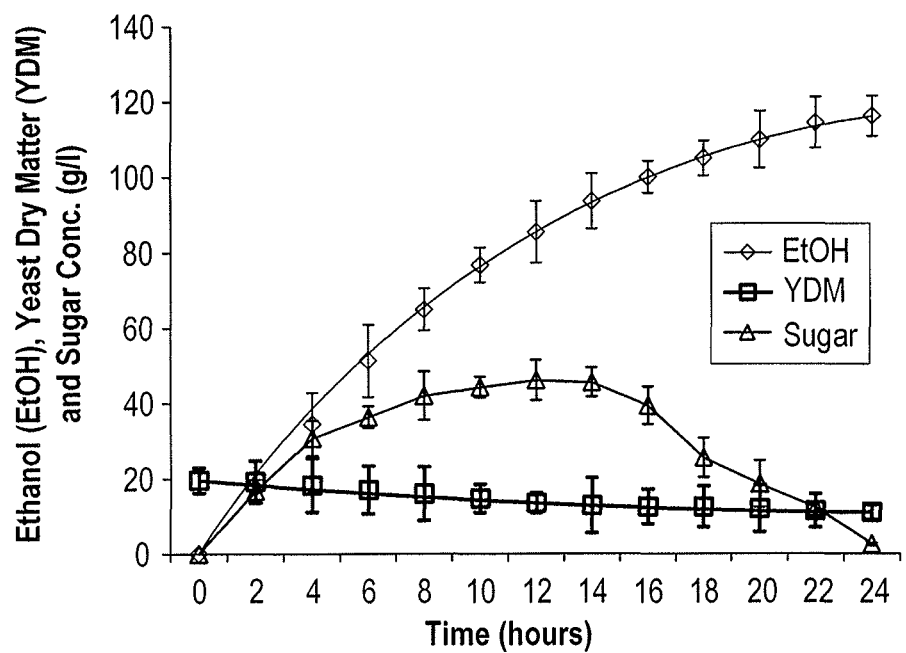
FIG. 19: depicts a graph of ethanol production from date extract and molasses (1:1) in fed-batch using the yeast S. cerevisiae NCYC 431.
Figure 20:
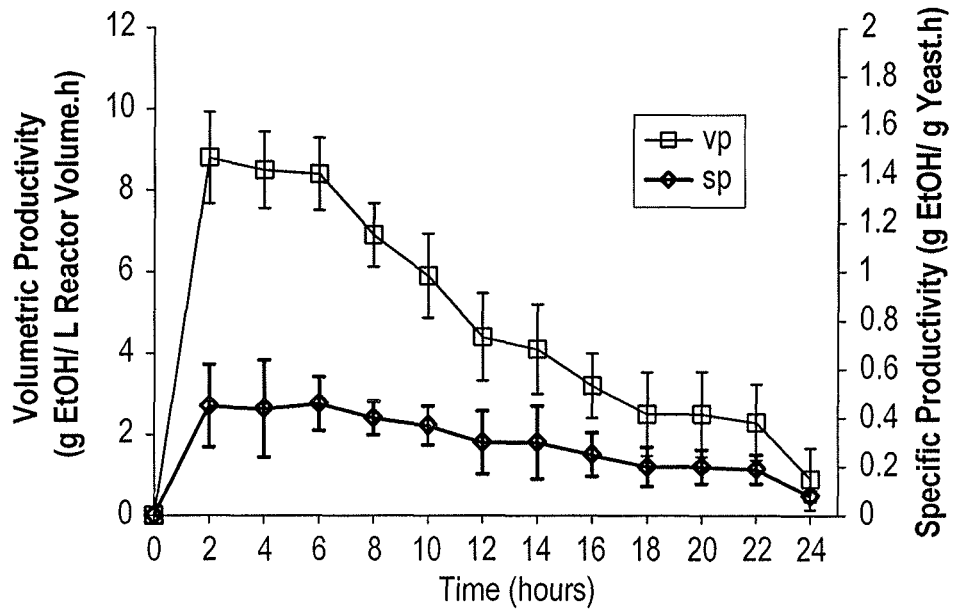
FIG. 20: depicts a graph of specific and volumetric productivities of ethanol from date extract and molasses (1:1) in fed-batch using the yeast S. cerevisiae NCYC 431.
Figure 21:
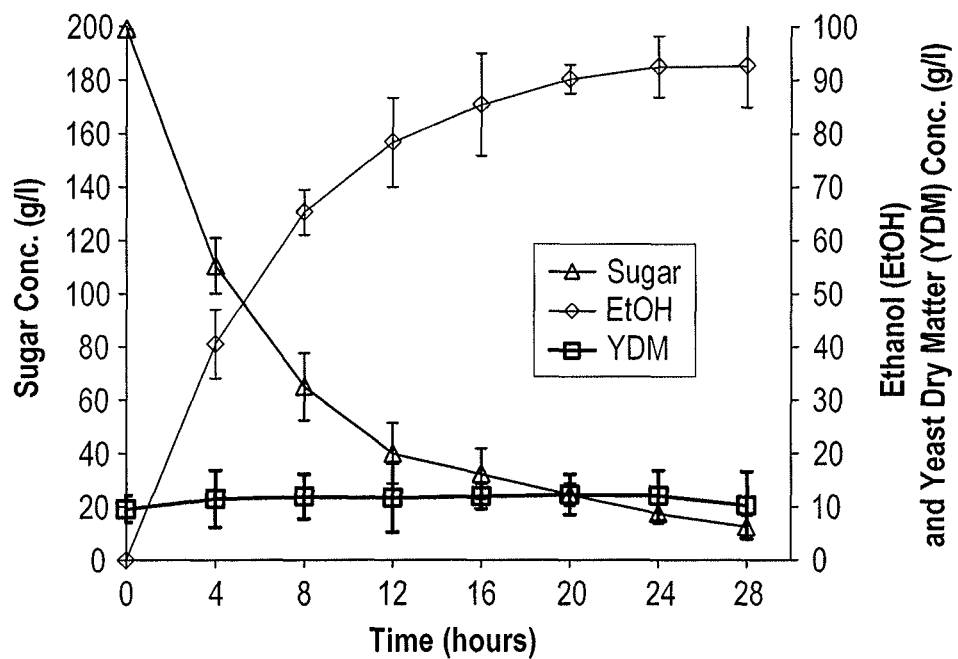
FIG. 21: depicts a graph of ethanol production from date extract in fed-batch using the yeast K. marxianus HH 5.

The substrate obtained from mixing date extract with molasses at a 1:1 ratio was utilized by the yeast in a similar efficiency as the former substrates discussed above (FIGS. 19 and 20). Ethanol concentration was 17.6 g/l after 2 hours of fermentation and reached 116.3 g/l (11.6% w/v) at the end of fermentation after 24 hours (FIG. 19). The specific productivity remained relatively high during the whole fermentation period at values of 0.45 and 0.2 g/g·h (FIG. 20). Sugar concentration increased slowly during substrate feeding, and then decreased quickly to reach traces at the end of fermentation (FIG. 19). No significant yeast growth occurred. The yield of ethanol on sugar was 95.1% of theoretical and was not significantly different from the yields of the other two substrates discussed above.

Date extract gave ethanol yields comparable to those obtained from the reference substrate molasses.

Example 8

Fermentation Testing with *K. marxianus* HH5

The strain *Kluyveromyces marxianus* HH5, isolated by the research team from local habitats in Saudi Arabia, was used for ethanol production in batch processes at fermentation temperatures of 40° C. on substrates of pure date extract, pure molasses and a 1:1 mixture of date extract and molasses. The results are shown in FIGS. 21 to 26.

Production in a substrate of date extract containing about 20% sugar started at a relatively high rate. Ethanol concentration reached 40.5 g/l in the first 4 hours, which is comparable to values obtained from the other yeasts described above (FIG. 21). Production continued at a reduced rate, and the maximum ethanol concentration was 92.7 g/l, reached in 24 hours of fermentation, which then remained almost constant till the end of fermentation after 28 hours. About 13 g/l sugar remained unconsumed in the fermentation broth and no significant increase in yeast concentration was observed. The yield of ethanol on sugar was 92.7% of the theoretical, which was quite good for a wild yeast strain. The yeast seemed to have converted most consumed sugars to ethanol without significant amounts of other metabolic products.

Figure 22:
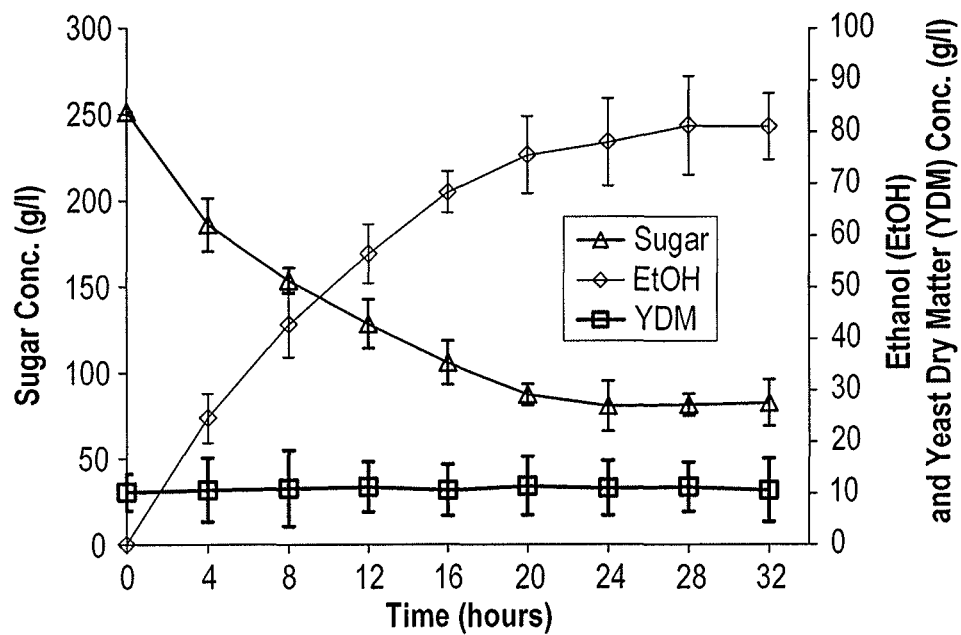
FIG. 22: depicts a graph of specific and volumetric productivities of ethanol from date extract in fed-batch using the yeast K. marxianus HH 5.

When a substrate of date extract containing about 25% sugar concentration was used, the rate of production decreased drastically. Only 24.5 g/l ethanol concentration was reached in the first 4 hours of fermentation compared to 40.5 g/l when 20% sugar concentration was used (FIG. 22). Production continued after that at a low rate and the highest ethanol concentration was 81.2 g/l, reached after 28 hours of fermentation, and no further increase in ethanol concentration was observed when fermentation time was extended to 32 hours. This suggests that this yeast is sensitive to high sugar concentration. The yield of ethanol on sugar was 64.7% of the theoretical, which was very low compared to the yield of 92.7% obtained when a 20% sugar concentration was used. Therefore, it can be concluded that this yeast can produce and tolerate up to about 9% w/v or 11% v/v ethanol concentration. This high productivity is particularly of interest given that it can be achieved at a fermentation temperature of 40° C. The combination of high productivity and higher fermentation temperature suggests that this method could reduce the costs of cooling during fermentation and heating during distillation.

Figure 23:
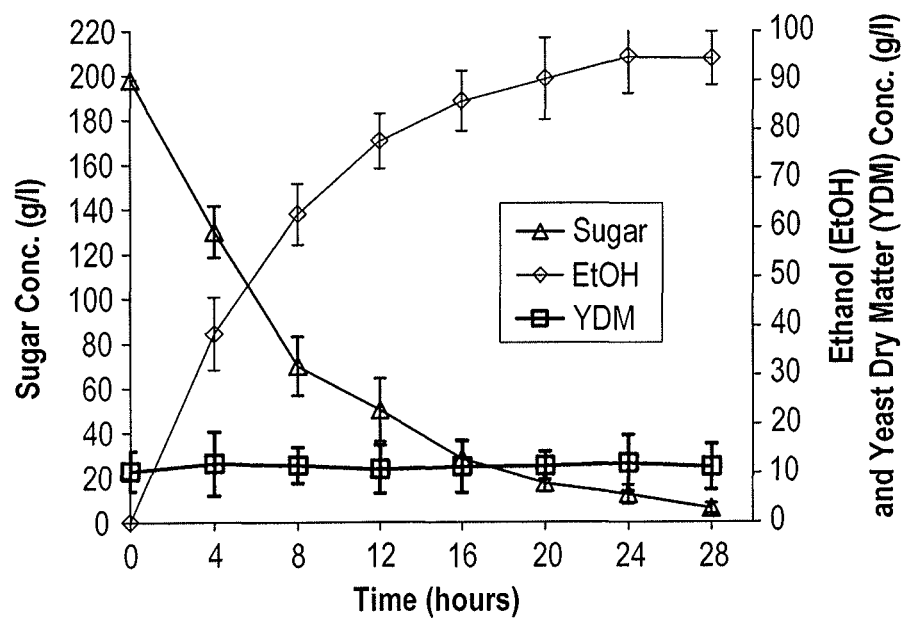
FIG. 23: depicts a graph of ethanol production from molasses in fed-batch using the yeast K. marxianus HH 5.
Figure 24:
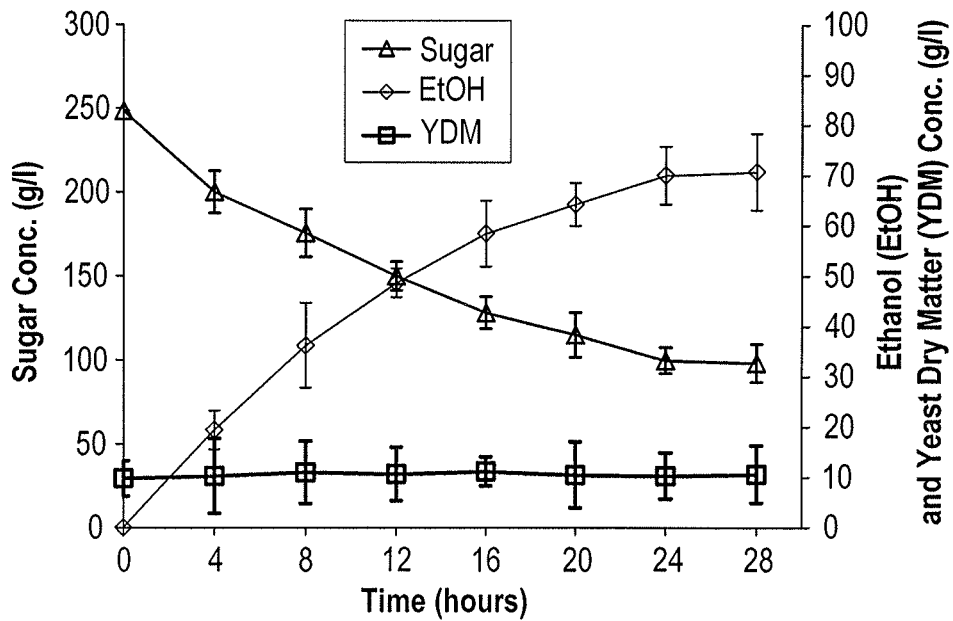
FIG. 24: depicts a graph of specific and volumetric productivities of ethanol from molasses in fed-batch using the yeast K. marxianus HH 5.

The yeast used molasses as substrate for ethanol production in a quite similar way as its use of date extract, confirming suitability of date extract as substrate for ethanol production. As can be seen in FIG. 23, ethanol concentration was 38.4 g/l after 4 hours of fermentation and reached 94.8 g/l in 24 hours then remained almost constant till 28 hours of fermentation. This result confirms that the yeast *K. marxianus* HH 5 can produce and tolerate ethanol concentrations in range of about 9-10% w/v (11-12% v/v). About 6 g/l sugar remained unconsumed and no significant yeast growth occurred. The yield of ethanol on sugar was 95.8% of the theoretical, which was higher than that obtained from date extract but the difference was not significant as statistical analysis showed. It is apparent that most of the sugar consumed was used for ethanol production and no significant amounts of other metabolic products were formed. When sugar concentration in the molasses substrate was raised to 25%, the performance of the yeast became very weak. The highest ethanol concentration reached was about 7.1% w/v (about 9% v/v) in 28 hours of fermentation, which was the lowest concentration obtained (FIG. 24). The yield of ethanol on sugar was only 56.9% of the theoretical, and about 98 g/l sugar remained unconsumed. This is a very low yield compared to the 95.8% obtained from molasses substrate containing 20% sugar, and confirms the result achieved when date extract substrate containing 25% sugar was used. This indicates again that the yeast *K. marxianus* HH 5 is sensitive to high sugar and ethanol concentrations.

Substrates of mixed date extract and molasses that contained 20% sugar gave a little lower substrate containing 20% sugar, and confirmed the result achieved when date extract substrate containing 25% sugar was used. This indicates again that the yeast *K. marxianus* HH 5 is sensitive to high sugar and ethanol concentrations.

Figure 25:
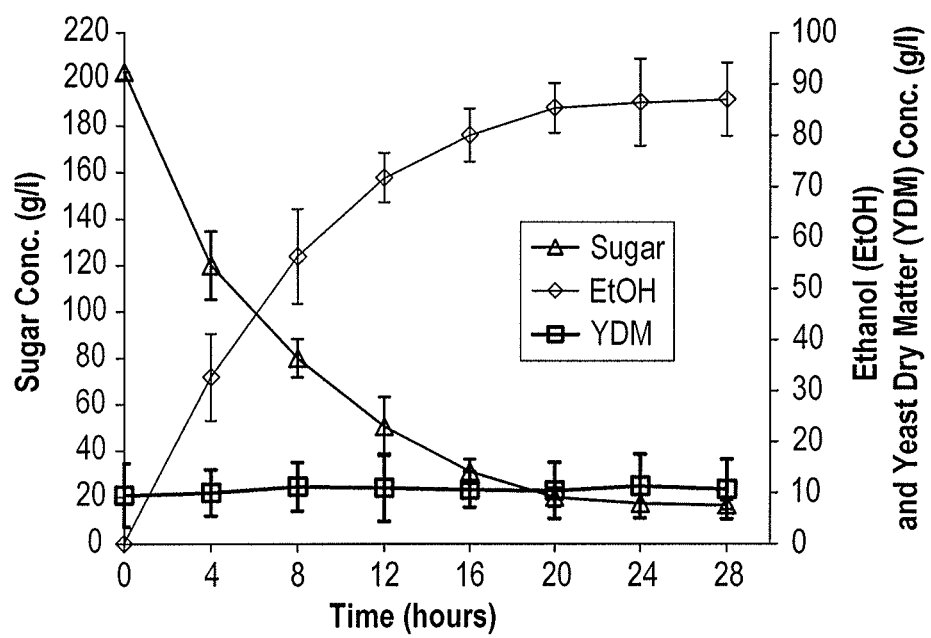
FIG. 25: depicts a graph of ethanol production from date extract and molasses (1:1) in fed-batch using the yeast S K. marxianus HH 5.
Figure 26:
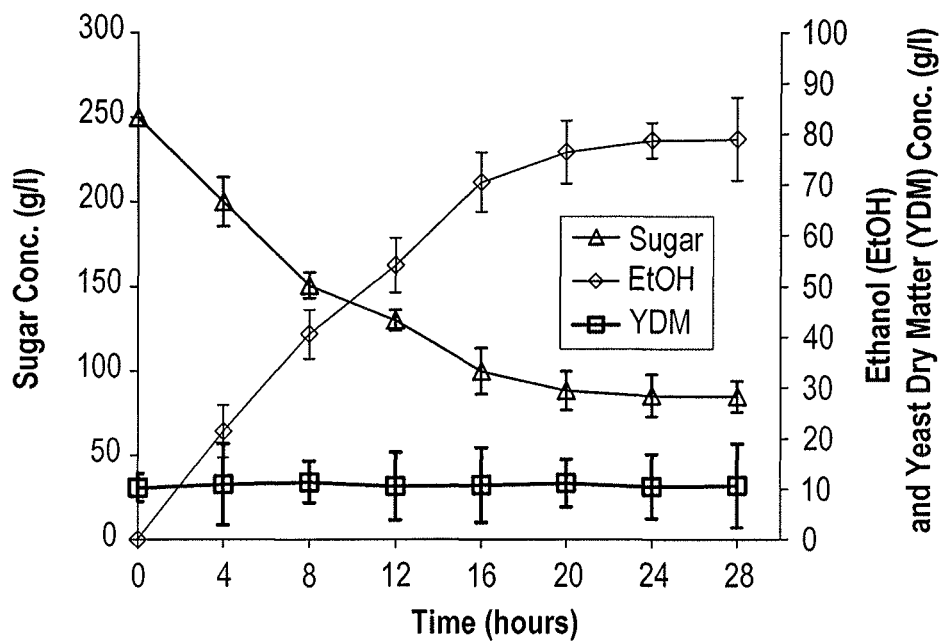
FIG. 26: depicts a graph of specific and volumetric productivities of ethanol from date extract and molasses (1:1) in fed-batch using the yeast K. marxianus HH 5.

Substrates of mixed date extract and molasses that contained 20% sugar gave a little lower ethanol yields compared to substrates of pure date extract and pure molasses containing the same sugar concentrations. The maximum ethanol concentration reached was 8.7% w/v (11% v/v) in 28 hours of fermentation and the yield of ethanol on sugar was 85.7% of the theoretical (FIG. 25). No considerable yeast growth occurred and about 17 g/l sugar remained in the fermentation broth unconsumed. In substrates containing sugar concentrations of about 25%, the yield of ethanol on sugar dropped to 63.3% of the theoretical compared to the 85.7% obtained from the substrates containing 20% sugar. The maximum ethanol concentration reached was 7.9 w/v (10% v/v) in 28 hours of fermentation (FIG. 26) with no significant yeast growth and about 85 g/l sugar remaining unconsumed.

It is to be understood that the method for producing bioethanol from dates is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method for producing bioethanol from dates, comprising:
   de-pitting date fruits to produce date fruit flesh;
   heating the date fruit flesh with water to produce a mixture;
   filter pressing the mixture to produce a juice;
   concentrating the juice to produce a date substrate, wherein the date substrate used for the fermentation has a starting sugar concentration ranging from 20% to 25%; and fermenting the date substrate with yeast at between 30° C.-40° C. for 32 hours, wherein the yeast is selected from the group consisting of *S. cerevisiae* and *S. cerevisiae* NCYC 431, to produce a 11.2-11.8% w/v bioethanol concentration.

2. The method for producing bioethanol from dates according to claim 1, wherein heating the date fruit flesh comprises mixing the date fruit flesh with an equal volume of water at about 80° C. for about 30 minutes to produce the mixture.

3. The method for producing bioethanol from dates according to claim 1, further comprising further purifying the juice by micro-filtration using a sheet filter system before the juice is concentrated.

4. The method for producing bioethanol from dates according to claim 1, wherein concentrating the juice comprises vacuum drying the juice.

5. The method for producing bioethanol from dates according to claim 1, wherein the vacuum drying comprises vacuum drying the juice to about 75 Brix at a temperature of about 80° C.

6. The method for producing bioethanol from dates according to claim 1, wherein the date fruits comprise waste date fruits.

7. The method for producing bioethanol from dates according to claim 6, wherein the waste date fruits are selected from the group consisting of Ruzeiz, Shunaizi, and Shahal dates.

8. The method for producing bioethanol from dates according to claim 7, wherein the waste date fruits are harvested in Saudi Arabia.

9. The method for producing bioethanol from dates according to claim 1, wherein the fermenting comprises fermenting the date substrate in a batch culture.

10. The method for producing bioethanol from dates according to claim 1, wherein the fermenting comprises fermenting the date substrate in a fed-batch culture.

\* \* \* \* \*